US009645093B2

(12) United States Patent
Sullivan et al.

(10) Patent No.: US 9,645,093 B2
(45) Date of Patent: *May 9, 2017

(54) SYSTEM AND METHOD FOR APODIZATION IN A SEMICONDUCTOR DEVICE INSPECTION SYSTEM

(71) Applicant: KLA-Tencor Corporation, Milpitas, CA (US)

(72) Inventors: Jamie M. Sullivan, Eugene, OR (US); Gary Janik, Palo Alto, CA (US); Steve Cui, Fremont, CA (US); Rex Runyon; Dieter Wilk, San Jose, CA (US); Steve Short, San Jose, CA (US); Mikhail Haurylau, San Jose, CA (US); Qiang Q. Zhang, San Jose, CA (US); Grace Hsiu-Ling Chen, Los Gatos, CA (US); Robert M. Danen, San Jose, CA (US); Suwipin Martono, Castro Valley, CA (US); Shobhit Verma, Fremont, CA (US); Wenjian Cai, Sunnyvale, CA (US); Meier Brender, San Jose, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/930,254

(22) Filed: Nov. 2, 2015

(65) Prior Publication Data

US 2016/0054232 A1    Feb. 25, 2016

Related U.S. Application Data

(63) Continuation of application No. 13/760,829, filed on Feb. 6, 2013, now Pat. No. 9,176,069.

(Continued)

(51) Int. Cl.
*G01N 21/00* (2006.01)
*G02B 27/58* (2006.01)
(Continued)

(52) U.S. Cl.
CPC ..... *G01N 21/8806* (2013.01); *G01N 21/9501* (2013.01); *G01N 21/95623* (2013.01); *G02B 27/58* (2013.01); *G01N 2021/8825* (2013.01)

(58) Field of Classification Search
CPC ... G02B 27/58; G02B 21/004; G03F 7/70291; G01N 21/956
(Continued)

(56) References Cited

U.S. PATENT DOCUMENTS

| 363,961 | A | * | 5/1887 | Kuhn | G03B 17/12 |
| | | | | | 396/545 |
| 3,977,772 | A | * | 8/1976 | Rimmer | G02B 27/58 |
| | | | | | 359/739 |

(Continued)

FOREIGN PATENT DOCUMENTS

TW    201200974 A    1/2012

*Primary Examiner* — Roy M Punnoose
(74) *Attorney, Agent, or Firm* — Suiter Swantz pc llo

(57) ABSTRACT

An inspection system with selectable apodization includes a selectably configurable apodization device disposed along an optical pathway of an optical system. The apodization device includes one or more apodization elements operatively coupled to one or more actuation stages. The one or more actuation stages are configured to selectably actuate the one or more apodization elements along one or more directions. The inspection system includes a control system communicatively coupled to the one or more actuation stages. The control system is configured to selectably control an actuation state of at the one or more apodization elements so as to apply a selected apodization profile formed with the one or more apodization elements.

46 Claims, 20 Drawing Sheets

Related U.S. Application Data

(60) Provisional application No. 61/597,459, filed on Feb. 10, 2012.

(51) Int. Cl.
*G01N 21/88* (2006.01)
*G01N 21/95* (2006.01)
*G01N 21/956* (2006.01)

(58) Field of Classification Search
USPC .......................................... 356/237.3, 237.5
See application file for complete search history.

(56) References Cited

U.S. PATENT DOCUMENTS

| | | | | |
|---|---|---|---|---|
| 4,030,817 A * | 6/1977 | Westell | ................... | G02B 27/58 356/216 |
| 4,537,475 A * | 8/1985 | Summers | ............... | G02B 27/58 359/559 |
| 5,619,266 A * | 4/1997 | Tomita | ................. | H04N 5/2353 348/221.1 |
| 5,859,424 A | 1/1999 | Norton et al. | | |
| 6,020,957 A | 2/2000 | Rosengaus et al. | | |
| 6,248,988 B1 | 6/2001 | Krantz | | |
| 6,259,055 B1 * | 7/2001 | Sokol | ................. | B23K 26/0069 219/121.68 |
| 6,656,373 B1 * | 12/2003 | Neal | ........................ | G01J 9/00 216/12 |
| 6,882,417 B2 | 4/2005 | Goldberg et al. | | |
| 7,030,978 B2 | 4/2006 | Guetta et al. | | |
| 7,053,999 B2 | 5/2006 | Goldberg et al. | | |
| 7,145,654 B2 | 12/2006 | Norton | | |
| 7,173,694 B2 | 2/2007 | Goldberg et al. | | |
| 7,245,347 B2 * | 7/2007 | Lundgren | ............... | G02B 5/005 349/200 |
| 7,317,527 B1 | 1/2008 | Maciuca et al. | | |
| 7,397,557 B2 | 7/2008 | Jeong et al. | | |
| 7,460,221 B2 | 12/2008 | Goldberg et al. | | |
| 7,471,435 B2 * | 12/2008 | Modavis | ................ | G02B 27/58 359/227 |
| 7,535,563 B1 | 5/2009 | Chen et al. | | |
| 7,580,559 B2 * | 8/2009 | Latypov | ............... | G03F 7/70291 359/290 |
| 7,619,735 B2 | 11/2009 | Milshtein | | |
| 7,705,963 B2 * | 4/2010 | Sandstrom | .......... | G03F 7/70091 250/559.05 |
| 7,869,020 B1 | 1/2011 | Lee | | |
| 7,929,220 B2 * | 4/2011 | Sayag | .................... | G02B 5/005 359/241 |
| 7,940,384 B2 | 5/2011 | Hill et al. | | |
| 8,373,919 B2 * | 2/2013 | Foller | ...................... | G03B 9/02 359/267 |
| 8,413,080 B1 * | 4/2013 | Somerstein | ......... | G03F 7/70091 716/51 |
| 8,441,639 B2 * | 5/2013 | Kandel | ................ | G01N 21/956 356/369 |
| 9,176,069 B2 * | 11/2015 | Sullivan | ............. | G01N 21/9501 |
| 2003/0137659 A1 * | 7/2003 | Milshtein | .......... | G01N 21/8806 356/237.2 |
| 2003/0179370 A1 | 9/2003 | Goldberg et al. | | |
| 2004/0060903 A1 * | 4/2004 | Neal | ........................ | G01J 9/00 216/41 |
| 2005/0073684 A1 | 4/2005 | Norton | | |
| 2005/0168790 A1 * | 8/2005 | Latypov | ............... | G03F 7/70291 359/239 |
| 2006/0056028 A1 | 3/2006 | Wildnauer | | |
| 2006/0152717 A1 | 7/2006 | Goldberg et al. | | |
| 2007/0258071 A1 * | 11/2007 | Case | ................... | G03F 7/70283 355/53 |
| 2011/0069312 A1 | 3/2011 | Kandel et al. | | |
| 2013/0114085 A1 * | 5/2013 | Wang | .................... | G01N 21/55 356/445 |
| 2013/0229661 A1 | 9/2013 | Kandel et al. | | |

* cited by examiner

SYSTEM AND METHOD FOR APODIZATION IN A SEMICONDUCTOR DEVICE INSPECTION SYSTEM

CROSS-REFERENCE TO RELATED APPLICATION

The present application is related to and claims the benefit of the earliest available effective filing date(s) from the following listed application(s) (the "Related Applications") (e.g., claims earliest available priority dates for other than provisional patent applications or claims benefits under 35 USC §119(e) for provisional patent applications, for any and all parent, grandparent, great-grandparent, etc. applications of the Related Application(s)).

RELATED APPLICATIONS

For purposes of the USPTO extra-statutory requirements, the present application constitutes a continuation patent application of United States Non-Provisional Patent Application entitled SYSTEM AND METHOD FOR APODIZATION IN A SEMICONDUCTOR DEVICE INSPECTION SYSTEM, filed Feb. 6, 2013, application Ser. No. 13/760,829, which is a regular (non-provisional) patent application of United States Provisional Patent Application, entitled SYSTEM AND METHOD FOR APODIZATION IN A SEMICONDUCTOR INSPECTION SYSTEM, filed Feb. 10, 2012, Application Ser. No. 61/597,459. All of the above-listed applications are incorporated herein by reference in the entirety.

TECHNICAL FIELD

The present invention generally relates to a method and system for implementing a selected apodizing function, and, in particular, a method and system for selectably implementing an apodizing function.

BACKGROUND

Fabricating semiconductor devices such as logic and memory devices typically includes processing a substrate such as a semiconductor wafer using a large number of semiconductor fabrication processes to form various features and multiple levels of the semiconductor devices. Examples of semiconductor fabrication processes include, but are not limited to, lithography, chemical-mechanical polishing, etch, deposition, and ion implantation. Multiple semiconductor devices may be fabricated in an arrangement on a single semiconductor wafer and then separated into individual semiconductor devices.

As the dimensions of semiconductor devices decrease, the demand for improved inspection processes and tools increases. Inspection processes are used at various steps during a semiconductor manufacturing process to detect defects on wafers, leading to increased device yield. Many different types of inspection tools have been developed for the inspection of semiconductor wafers. Defect inspection is currently performed using techniques such as bright field (BF) imaging, dark field (DF) imaging, and scattering. The type of inspection tool that is used for inspecting semiconductor wafers may be selected based on, for example, characteristics of the defects of interest and characteristics of the wafers that will be inspected. For example, some inspection tools are designed to inspect unpatterned semiconductor wafers or patterned semiconductor wafers.

Patterned wafer inspection is of particular interest and importance to the semiconductor industry because processed semiconductor wafers usually have a pattern of features formed thereon. Inspection of patterned wafers is, therefore, important to accurately detect defects that may have been formed on the wafer during, or as a result of, processing.

Many inspection tools have been developed for patterned wafer inspection. For example, patterned wafer inspection tools commonly utilize spatial filters to enhance patterned wafer inspection. These spatial filters may include, but are not limited to, Fourier filters and apodizing filters.

Since the light scattered from patterned features depends on various characteristics of the patterned features such as lateral dimension and period, the design of the spatial filter also depends on such characteristics of the patterned features. As a result, the spatial filter must be designed based on known or determined characteristics of the patterned features and must vary as different patterned features are being inspected. Therefore, it is desirable to provide a system and method that cures the defects of the prior art.

SUMMARY

An inspection system for providing selectable apodization is disclosed, in accordance with an embodiment of the present disclosure. In one embodiment, the inspection system includes an illumination source configured to illuminate a surface of a sample disposed on a sample stage. In another embodiment, the inspection system includes a detector configured to detect at least a portion of light emanating from the surface of the sample, the illumination source and the detector being optically coupled via an optical pathway of an optical system including an illumination arm and a collection arm. In another embodiment, the inspection system includes a selectably configurable apodization device disposed along the optical pathway of the optical system, wherein the apodization device includes one or more apodization elements operatively coupled to one or more actuation stages, the one or more actuation stages configured to selectably actuate the one or more apodization elements along one or more directions in order to apply a selected apodization profile.

An inspection system for providing apodization is disclosed, in accordance with another embodiment of the present disclosure. In one embodiment, the inspection system includes an illumination source configured to illuminate a surface of a sample disposed on a sample stage. In another embodiment, the inspection system includes a detector configured to detect at least a portion of light emanating from the surface of the sample. In another embodiment, the inspection system includes an optical system including an optical pathway configured to optically couple the illumination source and the detector. In another embodiment, the inspection system includes a serrated aperture assembly disposed along the optical pathway of the optical system and configured as an aperture of the optical system, the serrated aperture assembly including one or more serrated aperture stops, wherein at least some of the one or more serrated aperture stops include a plurality of serration features, the one or more serrated aperture stops including a serrated pattern having a selected orientation, wherein the one or more serrated aperture stops apply a selected apodization profile to illumination transmitted along the optical pathway of the optical system.

An inspection system for providing apodization is disclosed, in accordance with another embodiment of the present disclosure. In one embodiment, the inspection system includes an illumination source configured to illuminate a surface of a sample disposed on a sample stage. In another embodiment, the inspection system includes a detector configured to detect at least a portion of light emanating from the surface of the sample. In another embodiment, the inspection system includes an optical system including an optical pathway configured to optically couple the illumination source and the detector. In another embodiment, the inspection system includes a Fourier filter disposed along the optical pathway of the optical system, wherein the Fourier filter includes one or more illumination blocking elements arranged in an array pattern, wherein the one or more illumination blocking elements are arranged to block a portion of illumination from the sample, wherein one or more edge regions of the illumination blocking elements have a graduated transmission function, wherein a locally averaged transmission function of the Fourier filter is an apodizing function.

An inspection system for providing apodization is disclosed, in accordance with another embodiment of the present disclosure. In one embodiment, the inspection system includes a selectably configurable apodization device disposed along the optical pathway of the optical system, wherein the apodization device includes one or more apodization elements operatively coupled to one or more actuation stages, the one or more actuation stages configured to selectably actuate the one or more apodization elements along one or more directions. In another embodiment, the inspection system includes a control system communicatively coupled to the one or more actuation stages, wherein the control system is configured to selectably control an actuation state of at the one or more apodization elements, the selected apodization profile formed with the one or more apodization elements.

It is to be understood that both the foregoing general description and the following detailed description are exemplary and explanatory only and are not necessarily restrictive of the invention as claimed. The accompanying drawings, which are incorporated in and constitute a part of the specification, illustrate embodiments of the invention and together with the general description, serve to explain the principles of the invention.

BRIEF DESCRIPTION OF THE DRAWINGS

The numerous advantages of the disclosure may be better understood by those skilled in the art by reference to the accompanying figures in which.

DETAILED DESCRIPTION OF THE INVENTION

Figure 1A:
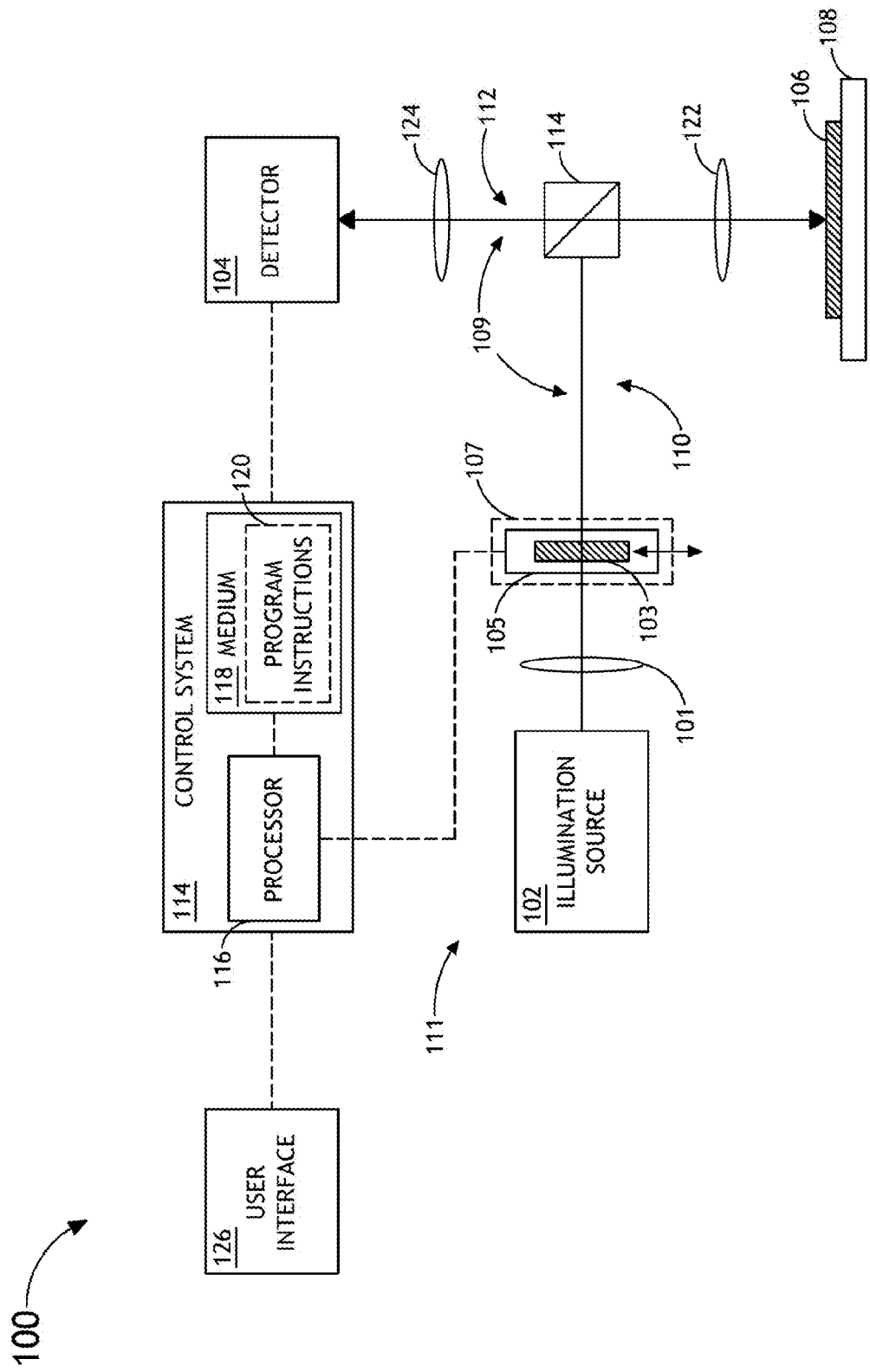
FIG. 1A is a simplified schematic view of a system for providing selectable apodization in a brightfield inspection system, in accordance with one embodiment of the present invention.

Reference will now be made in detail to the subject matter disclosed, which is illustrated in the accompanying drawings.

Referring generally to FIGS. 1A through 4F, systems and methods for implementing apodization in an optical pathway of an optical inspection system are described in accordance with the present disclosure.

The present invention is generally directed to methods and systems for providing apodization of illumination transmitted along an optical pathway of an inspection system used in the optical inspection of a sample, such as semiconductor wafer. Generally, apodization includes the modification of the amplitude transmittance of an aperture of an optical system in order to reduce diffraction effects. In the case of a circular aperture, apodization may consist of modifying the transmittance of the aperture in order to reduce or suppress the energy in the diffraction rings (relative to that of the central Airy disk). In the case of a non-circular aperture, the diffraction point spread function at an optical system's focal plane will not possess the form of an Airy pattern, but it will generally exhibit diffraction tails extending outside of the central diffraction peak as a result of diffraction at the aperture. For example, Born et al. describes apodization generally in Chapter 8 of *Principles of Optics*, 6th Ed., (1980), which is incorporated herein by reference in the entirety. The diffraction tails are commonly associated with the high spatial frequency component of two-dimensional transmittance profile of the aperture. The high spatial frequency component originates primarily from the sharp transmittance discontinuities at the aperture edges, and the diffraction tails can be suppressed by modifying the amplitude transmittance of the aperture, thereby mitigating these discontinuities. An aperture transmittance function which achieves this suppression of diffraction effects is referred to herein as an "apodization profile" or "apodization function." Common apodization functions include, but are not limited to, truncated Gaussian profiles and cosine profiles. The following disclosure provides multiple embodiments of methods and systems suitable for applying apodization to illumination transmitted along an optical pathway of an inspection system.

In addition, it is noted herein that patterned bus regions of semiconductor devices of a wafer are commonly very bright relative to well filtered array areas and unpatterned regions of the devices. Inspection tools are typically able to find much smaller defects in these well filtered array and unpatterned regions because less nuisance light is reflected or scattered from a pattern.

Unintentional optical artifacts in these quiet regions can limit the sensitivity of wafer inspection tools as these artifacts may result in false defects or increased noise levels. Optical artifacts can result from a number of sources including, but not limited to, diffraction from optical apertures. Diffraction can occur as a result of filtering mechanisms (e.g., Fourier filters) placed at the Fourier plane and used to filter diffraction orders from repetitive features. Diffraction artifacts can also occur from the limiting system apertures. In this setting bright features can "ring" into the unpatterned or well filtered array regions, limiting inspection sensitivity. The present invention is further directed to methods and systems for reducing optical artifacts or ringing from optical apertures of an inspection system.

FIG. 1A illustrates a simplified schematic view of an inspection system 100 with selectable apodization, in accordance with one embodiment of the present invention. The present invention is directed to a system and method providing a flexible means for enhancing resolution of an optical measurement system, such as an inspection system. It is recognized herein that apodization applied in a given setting may be selected based on one or more sample features (e.g., device pattern features). As such, the present invention provides an inspection system equipped with selectable apodization, allowing a user to either manually or automatically implement a selected apodization profile in response to one or more sample features. It is further noted that the present invention allows for the selectable apodization of illumination along two directions independently (e.g., X-direction and Y-direction).

In one aspect of the present invention, the system 100 includes an illumination source 102 configured to illuminate a surface of a sample 106 (e.g., semiconductor wafer) disposed on a sample stage 108, a detector 104 (e.g., CCD, TDI, or PMT detector) configured to detect light emanating (e.g., scattered or reflected) from the surface of the sample 106. The illumination source 102 (e.g., broadband source or narrowband source) and the detector 104 are optically coupled via an optical pathway 109 of an optical system 111. In another aspect, the system 100 includes a selectably configurable apodization device 107 disposed along the optical pathway 109 of the optical system 111 of the inspection system 100. The system 100 may further include a control system 114 (e.g., computer control system equipped with one or more processors 116) communicatively coupled to the selectably configurable apodization device 107 and suitable for selectably controlling the apodization applied to illumination transmitted along the optical pathway 109 and through the apodization device 107.

In a further aspect of the present invention, the selectably configurable apodization device 107 may include one or more apodization elements 103 operatively coupled to on one or more actuation stages 105. In this regard, the one or more actuation stages 107 are configured to selectably actuate the one or more apodization elements 103 along one or more directions (e.g., X-direction or Y-direction). The control system 114 may be communicatively coupled to the one or more actuation stages 103 of the apodization device 107, thereby allowing the control system 114 to selectably control apodization (e.g., apply a selected apodization profile along a first and/or second direction) of illumination transmitted along the optical pathway 109 of the optical system in one or more directions by controlling an actuation state (e.g., positioned within optical pathway or positioned outside of optical pathway) of the one or more apodization elements 103.

In another aspect of the present invention, the optical pathway 109 of the optical system 111 may include an illumination arm 110 and a collection arm 112. In this manner, the illumination source 102 and the detector 104 may be optically coupled via the illumination arm 110 and the collection arm 112 of the optical system 111. Light may emanate from the illumination source 102 and travel along the illumination arm 110 to the surface of the sample 106. Light scattered or reflected from the sample 106 may then travel from the surface of the sample 106 to the detector 104 along the collection arm 112.

In one embodiment, the apodization device 107 is disposed along the illumination arm 110 of the optical system 111 of the inspection system 100, as shown in FIG. 1A. In an alternative embodiment, although not shown in FIG. 1A, the apodization device 107 is disposed along the collection arm 112 of the optical system 111 of the inspection system 100.

Figure 1B:
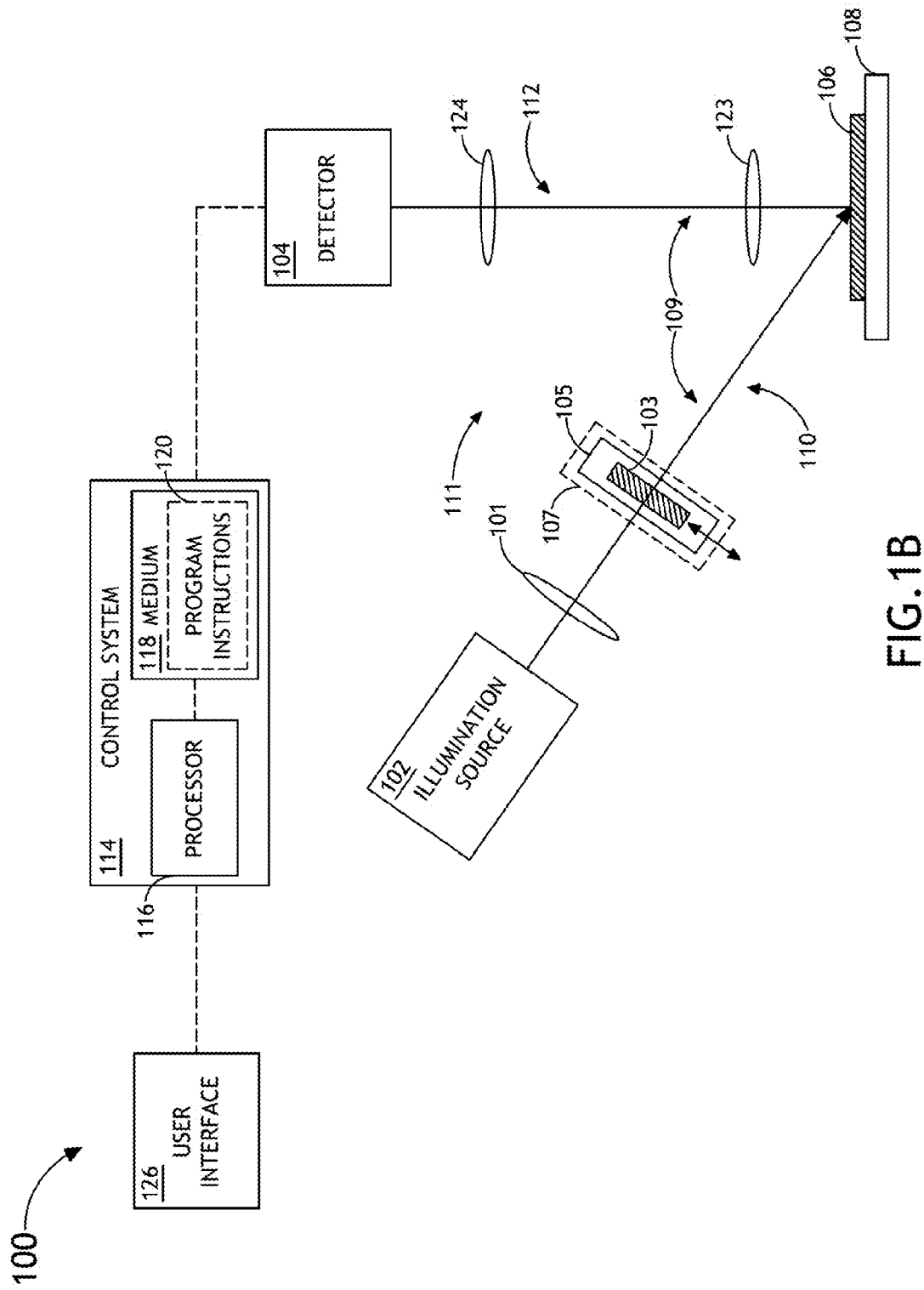
FIG. 1B is a simplified schematic view of a system for providing selectable apodization in a darkfield inspection system, in accordance with one embodiment of the present invention.

The inspection system of the present invention may be configured as any inspection system known in the art. For example, as shown in FIG. 1A, the inspection system 100 of the present invention may be configured as a bright field (BF) inspection system. Alternatively, as shown in FIG. 1B, the inspection system 100 of the present invention may be configured as a dark field (DF) inspection system. Applicant notes that the optical configurations depicted in FIGS. 1A and 1B are provided merely for illustrative purposes and should not be interpreted as limiting. In a general sense, the inspection system 100 of the present invention may include any set of imaging and optical elements suitable for imaging the surface of the wafer 106. Examples of currently available wafer inspection tools are described in detail in U.S. Pat. Nos. 7,092,082, 6,702,302, 6,621,570 and 5,805,278, which are each herein incorporated by reference. In addition, various embodiments of combination BF and DF inspection systems are provided in U.S. Pat. Nos. 5,822,055 and 6,201,601, which are each incorporated herein by reference in their entirety.

In additional embodiments, the illumination arm 110 and/or the collection arm 112 may include, but are not limited to, one or more additional optical elements as those skilled in the art should recognize that numerous optical elements may be utilized within the illumination arm 110 or collection arm 112 within the scope of the present invention. For example, in the case of the brightfield inspection system shown in FIG. 1A, the additional optical elements of the illumination arm 110 may include, but are not limited to, one or more condenser or focusing lenses 101, one or more objective lenses 122, one or more additional lenses, one or more beam splitters 114, one or more mirrors, one or more filters, one or more collimators and the like. Similarly, the optical elements of the collection arm 112 may include, but are not limited to, one or one or more imaging lenses 124, one or more additional lenses, one or more mirrors, one or more filters, or one or more collimators and the like.

In the case of the darkfield inspection system shown in FIG. 1A, the additional optical elements of the illumination arm 110 may include, but are not limited to, one or more focusing or condenser lenses 101, one or more additional lenses, one or more beam splitters (not shown), one or more mirrors, one or more filters, one or more collimators and the like. Similarly, the optical elements of the collection arm 112 may include, but are not limited to, one or more collection lenses 123, one or more imaging lenses 124, one or more additional lenses, one or more mirrors, one or more filters, or one or more collimators and the like. It is noted herein that the above described optical systems for the darkfield and brightfield embodiments of the inspection system 100 should not be interpreted as limiting. It is recognized herein that any implementing optical system will include additional optical elements not described herein. Applicant notes that the various additional elements were omitted from the present description for the purposes of clarity.

It is noted herein that while the following description of the present invention describes the inspection system 100, it is recognized herein that the apodization device 107 may be implemented in optical system not disclosed herein. As such, the particular optical configuration of system 100 should not be interpreted as limiting.

In another aspect of the present invention, the Illumination source 102 may include any broadband illumination source known in the art. In one embodiment, the illumination source 102 may include, but is not limited to, a halogen light source (HLS). For instance, the halogen light source may include, but is not limited to, a tungsten based halogen lamp. In another example, the illumination source 102 may include a xenon arc lamp. By yet another example, the illumination source 102 may include a deuterium arc lamp. In a general sense, any illumination source capable of producing illumination in the visible, infrared, and ultraviolet spectral ranges is suitable for implementation in the present invention. For example, a xenon arc lamp is capable of delivering light in a spectral range of 190 nm to 2000 nm, with a gradual radiant intensity decrease below 400 nm. In another embodiment, the illumination source 102 may include, but is not limited to, any discharge plasma source known in the art. In yet another embodiment, the illumination source 102 may include, but is not limited to, a laser-driven plasma source. It should be recognized by those skilled in the art that the above described illumination sources do not represent limitations, but should merely be interpreted as illustrative. In an additional aspect of the present invention, the illumination source 102 may include any narrowband illumination source known in the art. For example, the illumination source 102 may include, but is not limited to, one or more laser light sources.

It is noted that the above description relating to the various types of illumination sources should not be interpreted as limiting, but rather merely as illustrative. Those skilled in the art should recognize that any broadband or narrowband illumination source is suitable for implementation in the present invention. Moreover, it is further contemplated herein that two or more illumination source may be combined in order to achieve a required spectral range. In this manner, a first source emitting illumination in a first spectral range may be combined with a second source emitting illumination in a second spectral range. For example, a first light source may include a xenon lamp, while a second light source may include a deuterium lamp.

In another aspect of the present invention, the detector 104 may include any optical detection system known in the art suitable for imaging one or more features of the surface of the sample 106. In one embodiment, the detector 104 may include, but is not limited to, a CCD detector. In another embodiment, the detector 104 may include, but is not limited to, CCD-TDI detector. In another embodiment, the detector 103 may include but is not limited to, a PMT detector. In an additional embodiment, the detector 104 (e.g., imaging camera) may be communicatively coupled to an image processing computer which may identify and store imagery data acquired from the detector 104.

Referring now to the selectably configurable apodization device 107 of FIGS. 1A and 1B, the selectably configurable apodization device 107 may include any apodization element (e.g., apodizer) and actuation stage known in the art. For example, the selectably configurable apodization device 107 may include an apodization element 103 mechanically coupled to a linear translation stage (e.g., linear motorized stage). In this regard, the apodization element 103 is configured for the selective linear translation in to and out of the optical pathway 109 of the optical system 111 in response to a command signal received from the control system 114. By way of another example, the selectably configurable apodization device 107 may include an apodization element 103 mechanically coupled to a rotational stage (e.g., motorized rotational stage). In this regard, the apodization element 103 is configured for the selective rotation in to and out of the optical pathway 109 of the optical system 111 in response to a command signal received from the control system 114. By way of another example, the selectably configurable apodization device 107 may include an apodization element 103 mechanically coupled to a combination translational-rotational stage. In this regard, the apodization element 103 is configured for the selective rotation and/or translation in to and out of the optical pathway 109 of the optical system 111 in response to a command signal received from the control system 114.

In another aspect of the present invention, the selectably configurable apodization device 107 may include multiple apodizing elements, with each apodizing element 103 disposed on an individual actuation stage (e.g., translational stage or rotational stage). In this regard, the apodization device 107 may include a battery of apodizing elements 103, whereby the control system 114 is configured to selectably actuate a selected sub-set of the apodizing elements 103 into the optical pathway 109 of the inspections system 100 via the corresponding actuation stages 105 in order to achieve a selected apodization profile. In this regard, the selected apodization profile is formed using the combination of multiple apodizing elements.

For example, the control system 114 may selectably actuate a single apodizing element 103 into the optical pathway 109 via its corresponding actuation stage 105. By way of another example, the control system 114 may selectably actuate two or more apodizing elements 103 into the optical pathway 109 via their corresponding actuation stages 105. It is recognized herein that the choice of apodizing element 103 to be actuated into the optical pathway 109 may depend on the apodizing characteristics required of the inspection system (e.g., based on pattern features of sample) as well as the pre-loaded apodizing elements 103 of the apodization device 107.

Figure 1C:
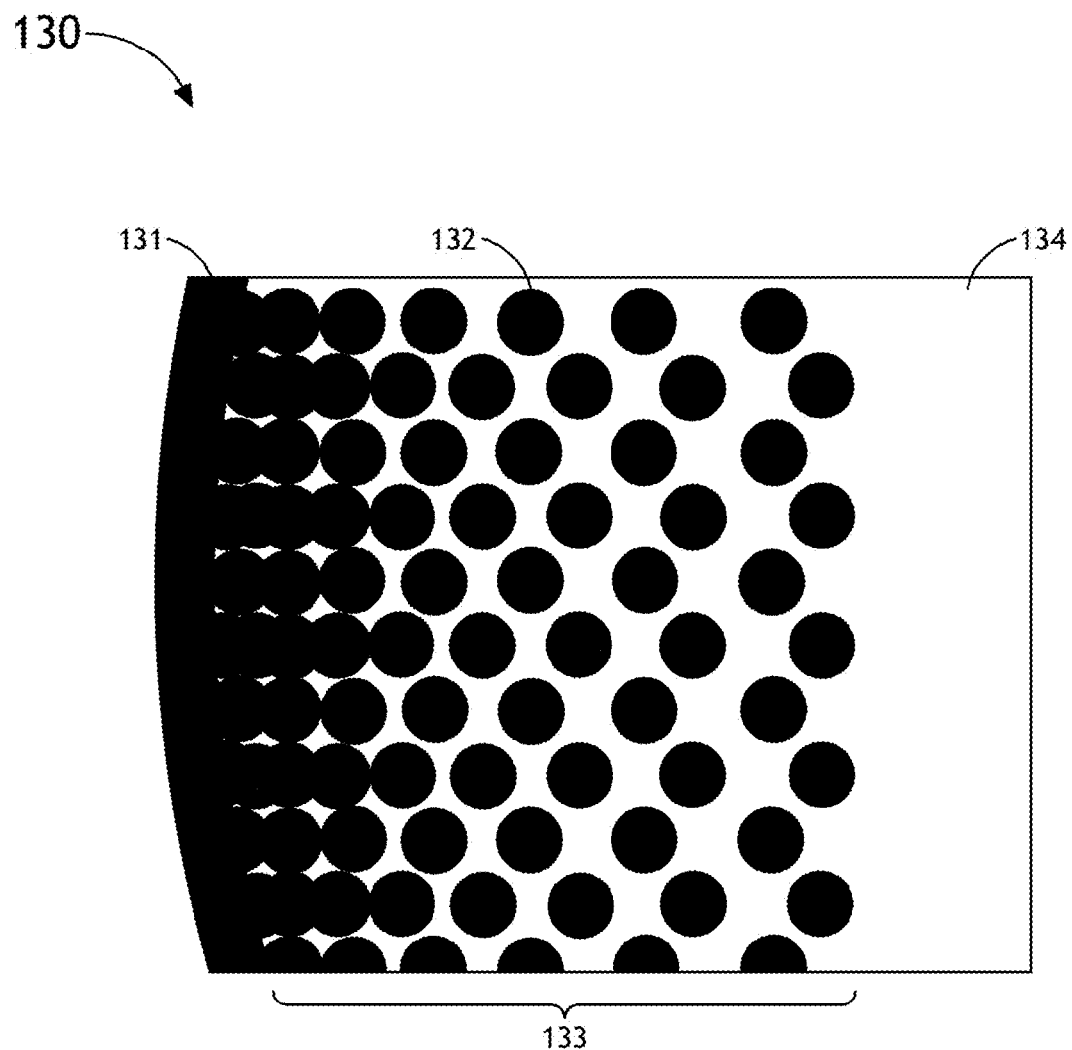
FIG. 1C is a schematic view of a section of a circular variable dot pattern density apodization element, in accordance with one embodiment of the present invention.

It is noted herein that any apodizing element or filter is suitable for implementation in the apodization device 107 of the present invention. In one embodiment, the one or more apodizing elements 103 of the apodization device 107 may include a variable dot density pattern element. FIG. 1C illustrates a segment of a variable dot density pattern element 130 configured for a circular aperture, in accordance with one embodiment of the present invention.

In one embodiment, the variable dot density based apodizing element 130 may include substantially opaque features 132, or "dots," on a substantially transparent background 134, whereby the density of the features varies as a function of the radial position on the apodizing element 130, as shown in FIG. 1C. In a further embodiment, the variable dot density pattern based apodizing element 103 may have a locally averaged transmittance function that is an apodizing function. In this regard, rather than a sharp transition from near 100% transmission to 0% transmission (e.g., typical microscope iris), the limiting aperture of the present embodiment may be lithographically printed with a series of opaque features of varying density. Further, in cases where the dot features are very dense, as is the case for the edge of the aperture, the transmission is very low. In contrast, when the density of features is very low as is the case for the center of the aperture 134, the transmission is very high. As shown in FIG. 1C, these varying feature density along the transition region 133 provides a smooth transition from the clear central part of the optical aperture 134 to the zero transmission limiting diameter position 131.

In an alternative embodiment, the variable dot density based apodizing element may include a "negative" version of the embodiment depicted in FIG. 1C. In this sense, the apodizing element 130 may include substantially transparent features on a substantially opaque background, whereby the density of the features varies as a function of the radial position on the apodizing element 130. It is recognized herein that the variable dot density apodizing elements 130 and random dot density apodizing elements of the present invention may be fabricated using any means known in the art. For example, the variable dot pattern or random dot pattern may be formed utilizing a lithographic printing, evaporation, and/or etching process. For instance, the opaque features of the apodizing element 130 (and negative version of element 130) may be lithographically printed onto a glass substrate. For instance, the opaque features may be formed from a metal material (e.g., chrome) deposited onto a substrate (e.g., glass substrate or quartz glass substrate). Applicants note that the above description of the variable dot density pattern is not limiting and is provided merely for illustration. It is anticipated that numerous geometrical configurations of the variable dot density element are suitable for implementation in the present invention. For example, it is noted herein that the dots of the dot density pattern are not limited to circles. The dots of the variable dot density pattern may include any geometrical shape known in the art, such as, but not limited to, rectangles, circles, ellipses, rings and the like.

In another embodiment, the one or more apodizing elements 103 of the apodization device 107 may include a spatially varying neutral density filter (not shown). U.S. Pat. No. 5,859,424 to Norton et al. describes the construction of individual apodizing filters (e.g., variable dot filters and neutral density filters) suitable for implementation in the apodization device 107 of the present invention and is incorporated herein by reference in the entirety.

In a further embodiment, the apodization device 107, when configured with the dot density (variable or random) or neutral coating density apodizing elements described above, may be positioned at any point along the optical pathway 109. In this regard, the apodization device 107 may be placed along the illumination arm 110 or the collection arm 112. For example, in the case of BF and/or DF inspection, the apodization device 107 may be positioned such that the active apodization element(s) 103 of the device 107 act as the limiting aperture stop (e.g., the illumination aperture stop) of the illumination arm 110, as conceptually shown in FIGS. 1A and 1B respectively. By way of another example, in the case of BF inspection, the apodization device 107 may be positioned at the imaging aperture stop of the collection arm 110, located prior to the imaging lens 124. By way of another example, in the case of DF inspection, the apodization device 107 may be positioned at the imaging aperture stop of the collection arm 110, located between the collection lens 123 and the imaging lens 124.

In another embodiment, the one or more apodizing elements 103 of the apodization device 107 may include, but are not limited, one or more serrated aperture stops configured as an aperture of the inspection system 100 and configured to apply an apodized pupil function. In this regard, when configured with a serrated aperture stop, the one or more apodization devices 107 may be positioned along the optical path 109 so as to serve as the aperture stop of the imaging system of the optical system 109. It is recognized herein that the imaging system of the optical system may reside in either the illumination arm 110 or the collection arm 112 of the inspection system 100. For example, the one or more apodizing elements 103 may consist of, but are not limited to, the serrated aperture stops described further herein and illustrated in FIGS. 3B, 3C, and 3F.

In another embodiment, the one or more apodizing elements 103 of the apodization device 107 may include, but are not limited, one or more Fourier filtering elements with edge apodization. In this regard, when configured with a Fourier filtering element, the one or more apodization devices 107 may be positioned along the optical path 109 so as to provide Fourier filtering of diffracted or reflected from patterned features from the sample. For example, when in a Fourier filtering configuration, the apodization device 107 may be positioned at the Fourier plane of the imaging system of the optical system 109. For instance, the apodization device 107 may be positioned at the Fourier imaging plane of the collection arm 112. For example, the one or more apodizing elements 103 may consist of, but are not limit to, the Fourier filter having one or more blocking elements with edge apodization described further herein and illustrated in FIGS. 4A-4F.

In one aspect of the present invention, the control system 114 may include one or more processors 116 communicatively coupled to the selectably configurable apodization device 107, as shown in FIGS. 1A-1B. For example, the one or more processors 116 of the control system 114 may be communicatively coupled to the one or more actuation stages 105 of the selectably configurable apodization device 104. In this regard, the control system 114 may consist of a computing system configured to control the selectably configurable apodization device 107 in order to achieve a selected apodization profile (as discussed throughout the present invention). In one embodiment, the one or more processors 116 of the control system 114 may act to configure the selectably configurable apodization device 107 into a selected apodization mode or state, thereby applying a selected apodization profile to illumination transmitted through the one or more apodizing elements 103.

In one embodiment, the apodization profile implemented by the one or more processors 116 of the control system 114 is a function of one or more patterns of the sample 106 being inspected by the inspection system 100. For example, in settings where a sample has a high DR, the one or more processors 116 of the control system 114 may apply an aggressive apodization profile (by actuating the corresponding apodization elements 103 need to achieve the aggressive profile) to illumination passing through the apodizing elements 103 of the selectably configurable apodization device 107. By way of another example, in settings where a sample has a low DR, the one or more processors 116 of the control system 114 may act to reduce the apodization by directing the one or more actuation stages 105 to withdraw one or more of the apodizing element 103 from the optical pathway 109.

In another embodiment, the one or more processors 116 of the control system 114 may selectably control apodization of illumination along a first direction and a second direction independently. For example, the one or more processors 116 of the control system 114 may direct the apodization device 107 to apply apodization to the X and Y axes independently. For instance, the amount of apodization applied may depend on the geometry of a layout of an inspected IC chip of the sample 106. Further, it is noted herein that for rectangular peripheral structures it may be desirable to apply only X apodization, while in other settings it may be desirable to apply only Y apodization.

In another embodiment, the one or more processors 116 of the control system 114 may selectably control apodization of illumination along the optical pathway 109 in one or more directions (e.g., X-direction or Y-direction) by controlling the actuation state of two or more actuation stages 105 of the selectably configurable apodization device 107. For example, a first apodization element may be disposed on a first actuation stage of the apodization device 107, while a second apodization element may be disposed on a second actuation stage of the apodization device 107. In this regard, the one or more processors 116 of the control system 114 are configured to selectably control the apodization profile of illumination transmitted along the optical pathway 109 of the optical system 111 in one or more directions by controlling an actuation state of the first apodization element and an actuation state of the second apodization element. It is noted herein that the above embodiment is not limited to two apodization elements. It is recognized herein that any number of apodizing elements and stages may be implemented in the selectably configurable apodization device 107 of the present invention. In addition, it is further noted that any type of apodization element (as described throughout the present disclosure) may be included in the multiple apodizing element selectably configurable apodization device 107 of the present invention.

In one embodiment, the one or more processors 116 of control system 114 may receive user inputted instructions via a user interface 126. In response to user inputted instructions, the one or more processors 116 of the control system 114 may act to configure the selectably configurable apodization device 107 into a selected apodization mode or state. For example, the one or more processors 116 of control system 114 may display a set of mode selections to a user via a display of the user interface. The user may then select one or more of the selections via a user input device (not shown). In response to this selection, one or more processors of the control system 114 may transmit control signals to the selectably configurable apodization device 107 in order to direct the one or more actuation stages 105 to actuate (e.g., translate or rotate) the one or more apodization elements 103 into or out of the optical pathway 109 in order to correspond with the user-selected configuration.

In another embodiment, the one or more processors 114 are in communication with a memory medium 118 (e.g., non-transitory storage medium). In addition, the one or more memory media 118 may store the program instructions configured to cause the one or more processors 116 to carry out the various steps described through the present disclosure. The memory medium 118 may include any memory medium known in the art including, but not limited to, a read-only memory, a random access memory, a magnetic or optical disk, or a magnetic tape. Program instructions 120 implementing methods such as those described herein may be transmitted over or stored on a carrier medium. The carrier medium may be a transmission medium such as a wire, cable, or wireless transmission link. The carrier medium may also include a memory medium 116 such as a read-only memory, a random access memory, a magnetic or optical disk, or a magnetic tape.

In general, the term "processor" may be broadly defined to encompass any device having one or more processors, which execute instructions from a memory medium. In this sense, the one or more processors 116 may include any microprocessor-type device configured to execute software algorithms and/or instructions. In one embodiment, the one or more processors 116 may consist of a desktop computer, a networked computer, an image computer, a work station, a parallel processing computer, and the like configured to execute a program configured to control the selectably configurable apodization device 107 of the system 100, as described throughout the present disclosure. It should be recognized that the steps described throughout the present disclosure may be carried out by a single computer system or, alternatively, multiple computer systems. Moreover, different subsystems of the system 100, such as the user interface 126, the actuation stages 105, and the like, may include a processor or logic elements suitable for carrying out at least a portion of the steps described above. Therefore, the above description should not be interpreted as a limitation on the present invention but merely an illustration.

In another embodiment, the one or more processors 116 of the control system 114 may be communicatively coupled to the selectably configurable apodization device 107, the illumination source 102, the detector 104, the user interface 126 or any other sub-system of system 100 in any manner known in the art. For example, the one or more processors 116 of the control system 114 may be communicatively coupled to the various sub-systems of system 100 via a wireline or wireless connection.

The user input device may include any user input device known in the art. For example, the user input device may include, but is not limited to, a keyboard, a keypad, a touchscreen, a lever, a knob, a scroll wheel, a track ball, a switch, a dial, a sliding bar, a scroll bar, a slide, a handle, a touch pad, a paddle, a steering wheel, a joystick, a bezel input device or the like. In the case of a touchscreen interface device, those skilled in the art should recognize that a large number of touchscreen interface devices may be suitable for implementation in the present invention. For instance, the display device may be integrated with a touchscreen interface, such as, but not limited to, a capacitive touchscreen, a resistive touchscreen, a surface acoustic based touchscreen, an infrared based touchscreen, or the like. In a general sense, any touchscreen interface capable of integration with the display portion of the display device is suitable for implementation in the present invention. In another embodiment, the user interface may include, but is not limited to, a bezel mounted interface. In the case of a bezel input device, the display device may include a bezel equipped with one or more bezel mounted interface devices. For instance, the bezel mounted interface may include, but is not limited to, a hard key (or hard "button") disposed on the bezel of the display device. In a general sense, any bezel mounted interface capable of integration with the display device is suitable for implementation in the present invention.

The display device of the user interface 126 may include any display device known in the art. In one embodiment, the display device may include, but is not limited to, a liquid crystal display (LCD). In another embodiment, the display device 104 may include, but is not limited to, an organic light-emitting diode (OLED) based display. In another embodiment, the display device 104 may include, but is not limited to a CRT display. Those skilled in the art should recognize that a variety of display devices may be suitable for implementation in the present invention and the particular choice of display device may depend on a variety of factors, including, but not limited to, form factor, cost, and the like. In a general sense, any display device capable of integration with a user interface device (e.g., touchscreen, bezel mounted interface, keyboard, mouse, trackpad, and the like) is suitable for implementation in the present invention.

It is recognized herein that while apodization of a pupil may lead to increased resolution in some settings, apodization may also carry with it penalties that render the implementation of such apodization undesirable. FIGS. 2A through 2F illustrate an analysis of optical conditions that may exist when determining whether apodization is desirable or undesirable.

Figure 2A:
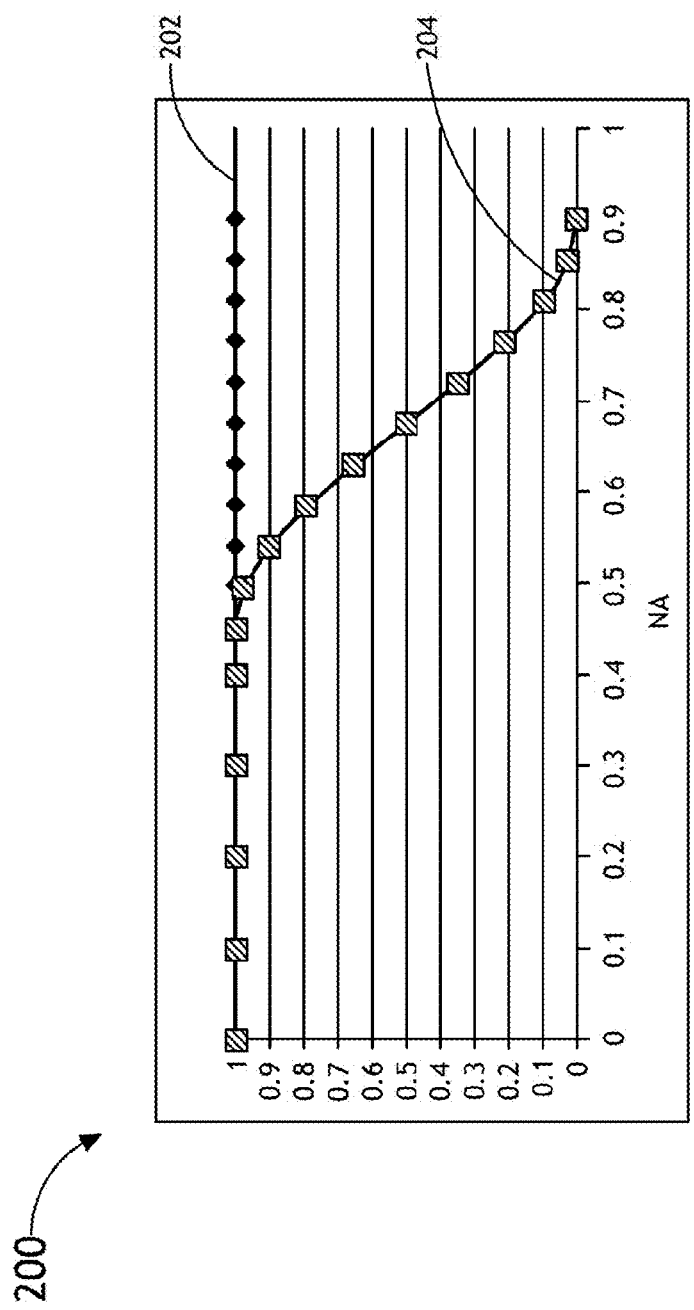
FIG. 2A is an intensity versus numerical aperture graph illustrating the intensity as a function of NA for an unapodized pupil and an apodized pupil, in accordance with one embodiment of the present invention.

FIG. 2A illustrates the transmission intensity profile of a cosine apodization filter 204 and the transmission intensity profile of an unapodized aperture 202. As shown in FIG. 2A, consider a 0.9 NA imaging system with a cosine profile applied from 0.45 NA to 0.9 NA. In this case, the pupil from 0 NA to 0.45NA is unapodized, and, therefore, displays no attenuation. For a uniformly illuminated pupil, the region from 0 NA to 0.45NA only contains approximately 25% of the overall illumination. Most of the illumination (approximately 75%) is contained in the region where apodization is applied. In the case of a cosine apodizing profile (see curve 204) applied from 0.45NA to 0.90NA, most of the illumination is blocked by the implemented apodizing filter. In this case, only 35% of the light from 0.45NA to 0.90NA is allowed to pass through the implemented apodizing filter. Further, over the entire aperture from 0 NA to 0.9NA, the optical system which is apodized from 0.45NA to 0.90NA loses approximately 50% of the available illumination. This represents a substantial apodizing filter implementation penalty.

Figure 2B:
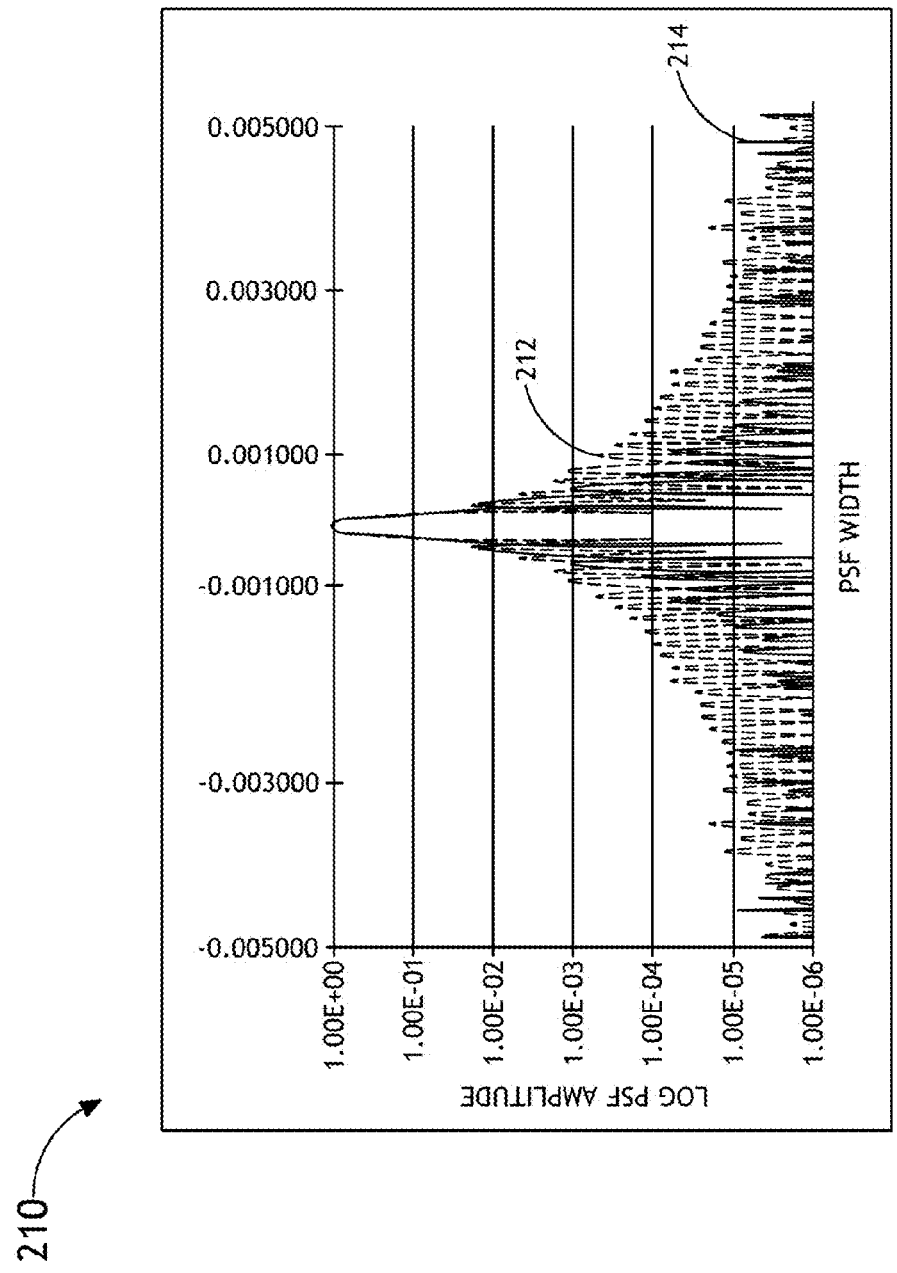
FIG. 2B is a log scale graph depicting the point spread function for an unapodized pupil and an apodized pupil, in accordance with one embodiment of the present invention.

Similarly, apodization elements/filters act to broaden the width of the point spread function measured at moderate fractions of the peak amplitude. Again, consider a system with a uniform pupil distribution from 0 NA to 0.45 NA with cosine apodization applied from 0.45NA to 0.9NA. Contrast this to a 0.9 NA optical system without apodization. Graph 210 of FIG. 1B illustrates a log plot of the PSF 212 as a function of PSF width for no apodization to the log plot of the PSF 214 for the cosine apodized setting described above. As shown in FIG. 2B, the application of the cosine apodizing filter acts to narrow the point spread function when measured at small fractions of the peak amplitude.

Figure 2C:
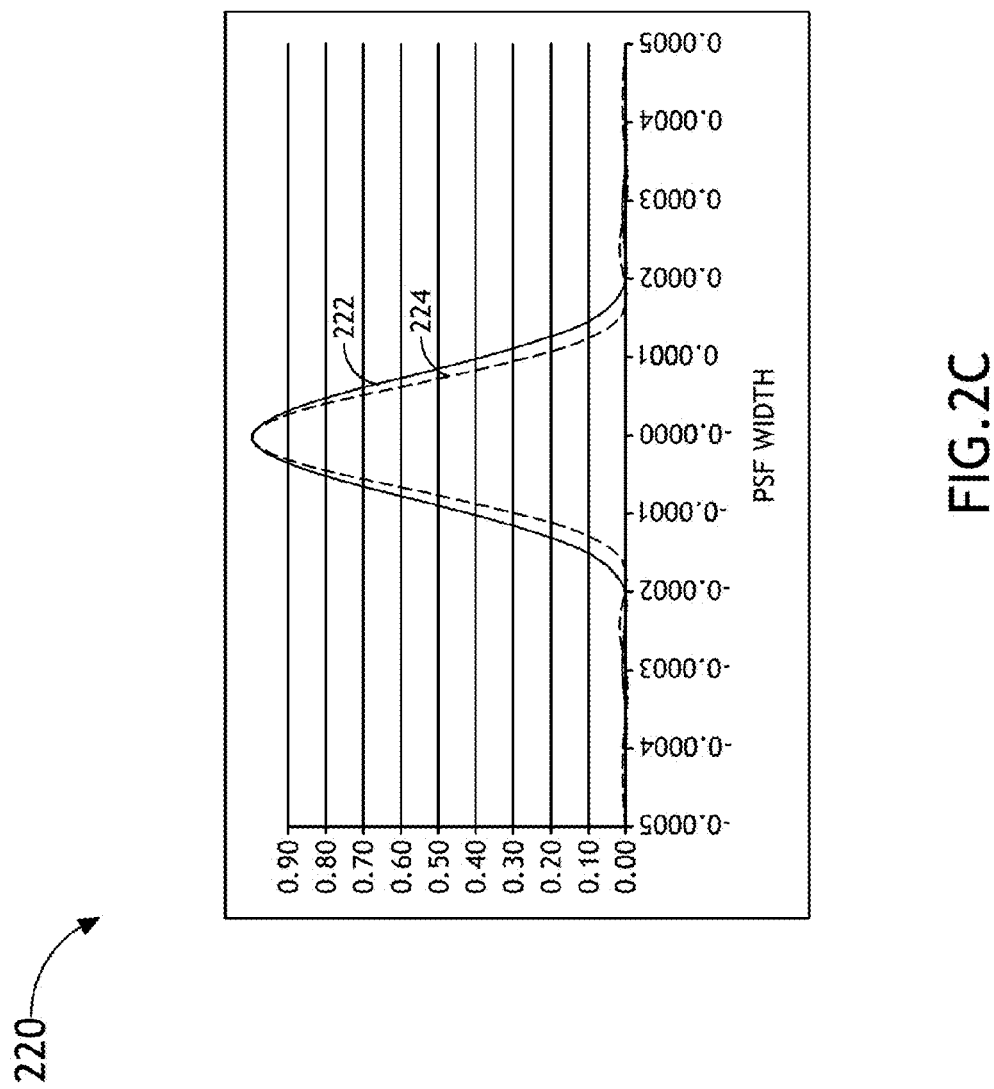
FIG. 2C is a linear scale graph depicting the point spread function for an unapodized pupil and an apodized pupil, in accordance with one embodiment of the present invention.
Figure 2D:
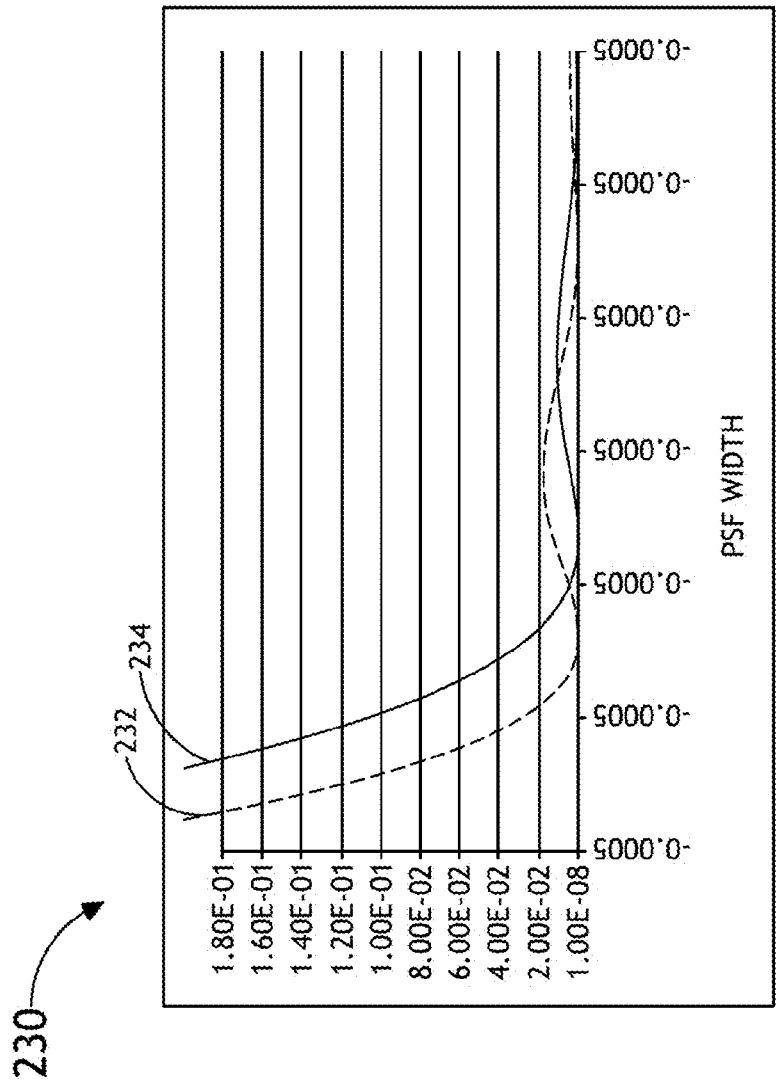
FIG. 2D is a linear scale graph depicting the point spread function for an unapodized pupil and an apodized pupil used to identify the first dark ring, in accordance with one embodiment of the present invention.

FIG. 2C illustrates a linear plot 220 of the point spread function for the apodized 222 and unapodized 224 configurations described above. Upon closer inspection of the point spread function from approximately 1.0 to 0.01, the PSF actually becomes wider upon adding the apodization function.

It is noted herein that Lord Rayleigh's criterion for resolution for uniform pupil distribution ($0.61 \cdot \lambda/NA$) calculates the location of the first dark ring. Utilizing the same point spread functions described above, the location of the first dark ring for uniform pupil distribution from 0 NA to 0.9NA with 266 nm light is found to be approximately 0.00018 mm, which matches the Rayleigh criterion. Further, the first dark ring for the case with uniform apodization from 0NA to 0.45NA and cosine apodization from 0.45 to 0.9NA is at 0.00022 mm, which is 20% wider than the unapodized configuration. It is recognized, therefore, that apodization may narrow the point spread function when control the tails of the point spread function is desirable, but it does so at the expense of the PSF width at modest fractions of the peak intensity.

For small defects, the peak signal from the defects is generally inversely proportional to square of the PSF width at moderate fractions of the peak. As a result, the use of apodization filters results in lower signals from smaller defects. In this case, the width of the PSF in the tails is not important to the signal from the small defect. In the case of unapodized systems, the bulk of the PSF may be concentrated into a smaller area. As a result, a higher fraction of the PSF interacts with the defect, which may lead to more scattered light for spot scanning imaging systems. In addition, it may result in more collected light focused onto fewer detector elements for a camera based imaging system. In both cases, the defect interacts with a larger fraction of the PSF. As a result of the broadening of the PSF, the signal will tend to decrease for apodized systems. While this may be a desirable trade off when these defects are in close proximity to very bright peripheral structures, it is not likely a desirable tradeoff in cases where defects are located in regions with little structure (e.g., bare areas and bulk array) that benefit from increased light.

It is further noted herein that a broadening of the central point spread function results in less resolution for logic regions. This behavior in effect acts to stop down the NA in order to improve the transition from very bright regions to very dark regions, which tends to negatively impact logic inspection ability. Again consider a cosine apodization from 0.45 to 0.9 NA. Such an apodization profile produced a first dark ring with radius of 0.00022 mm. It is noted that the equivalent unapodized system that would produce the same dark ring position would possess a NA of approximately 0.74.

Figure 2E:
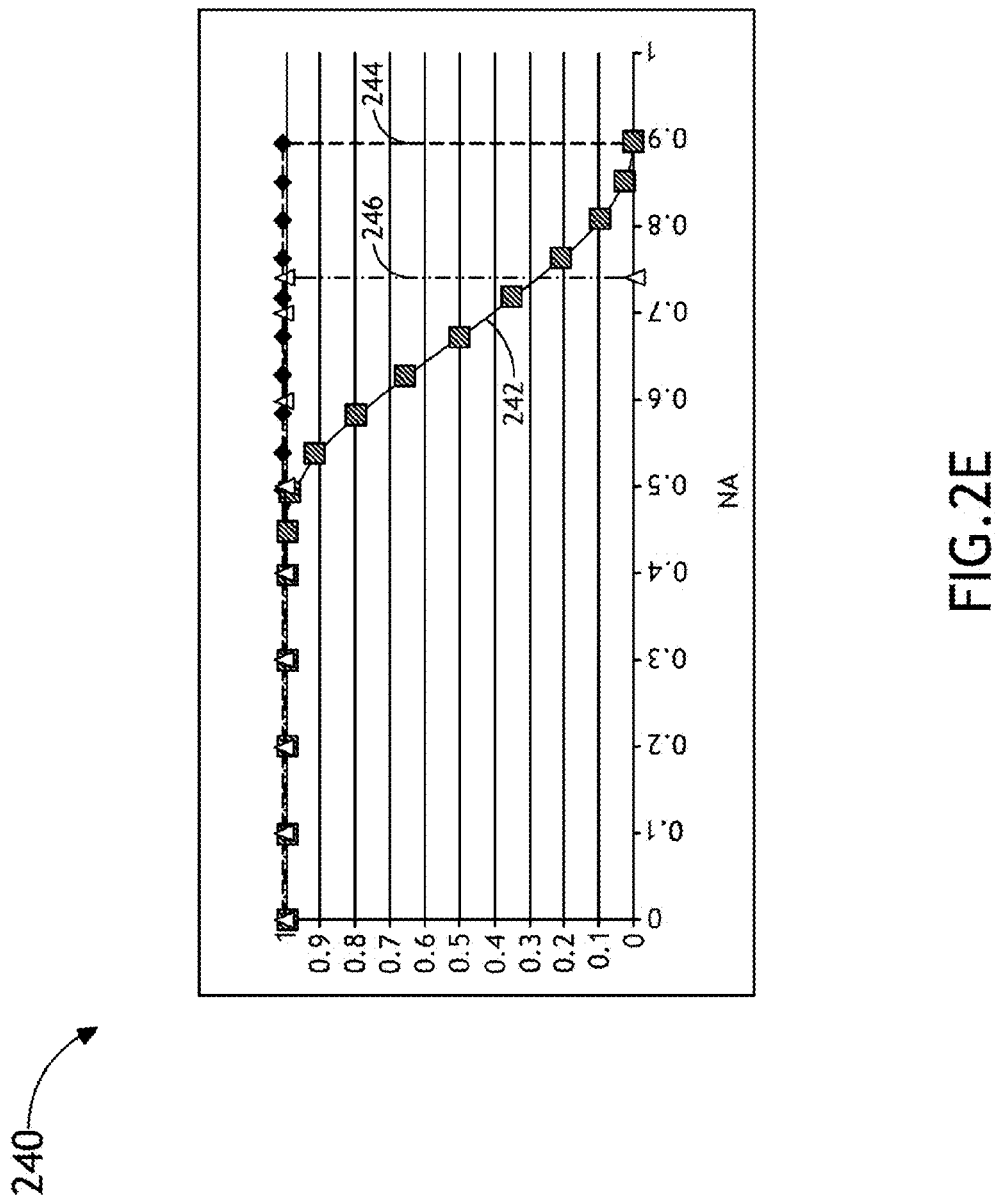
FIG. 2E is an intensity versus numerical aperture graph depicting intensity as a function of numerical aperture for various apodization profiles, in accordance with one embodiment of the present invention.

Graph 240 of FIG. 2E illustrates a pupil function 244 for uniform apodization from 0 to 0.9 NA, a pupil function 242 for cosine apodization from 0.45 to 0.9 NA, and a pupil function 246 for uniform apodization from 0 to 0.74 NA.

Figure 2F:
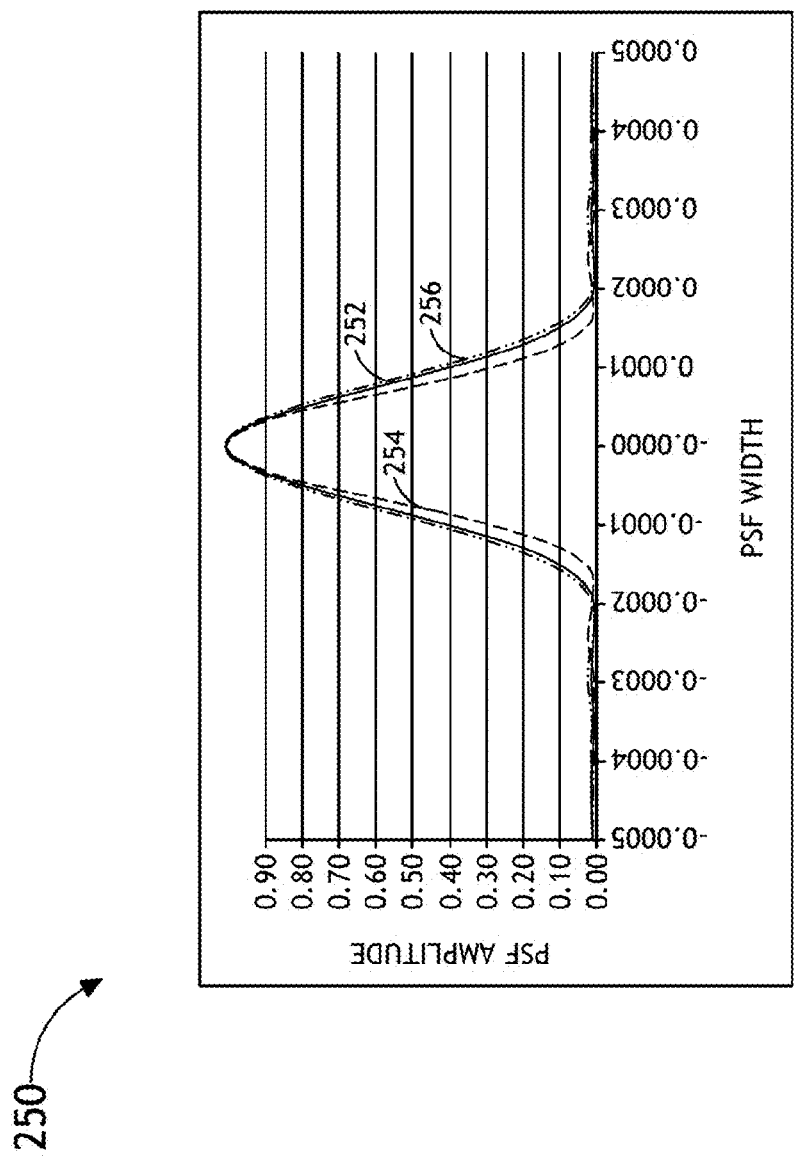
FIG. 2F is a linear scale graph depicting the point spread function for various apodization profiles, in accordance with one embodiment of the present invention.

Graph 250 of FIG. 2F illustrates PSF as function of PSF width 254 for uniform apodization from 0 to 0.9 NA, PSF as a function of PSF width 252 for cosine apodization from 0.45 to 0.9 NA, and PSF as a function of PSF width 256 for uniform apodization from 0 to 0.74 NA. As shown in FIG. 2F, the PSF for the "uniform from 0 to 0.45NA and cosine apodized from 0.45 to 0.9NA" configurations possess a very similar PSF width when compared to the "uniform 0 to 0.74NA" configuration when measured at moderate fractions of the peak.

As the various penalties above show, the analyzed pattern in question has a large impact on the decision as to whether apodization is desirable. It is recognized that apodization may be advantageous when trying to identify small defects in close proximity to very bright peripheral structures. In contrast, however, when the peripheral structures are not significantly brighter than the bulk array of the analyzed portion of the sample 106, the use of apodization and the corresponding penalties may inhibit the ability of system 100 to find defects.

For example, in the case where peripheral structures bordering array regions form a rectangular shape, it might be desirable to add apodization (using apodization device 107) to only a single axis. Similarly, if very bright vertical peripheral structures are present along with dim horizontal peripheral structures, a desired configuration may include apodization to the vertical axis only, leaving the horizontal axis unapodized.

In a general sense, it should be recognized that apodization of the pupil is not always desired. In this sense, the system 100 is configured to apply apodization selectively and is further configured to control the degree of strength of apodization when, in fact, implemented.

Figure 3A:
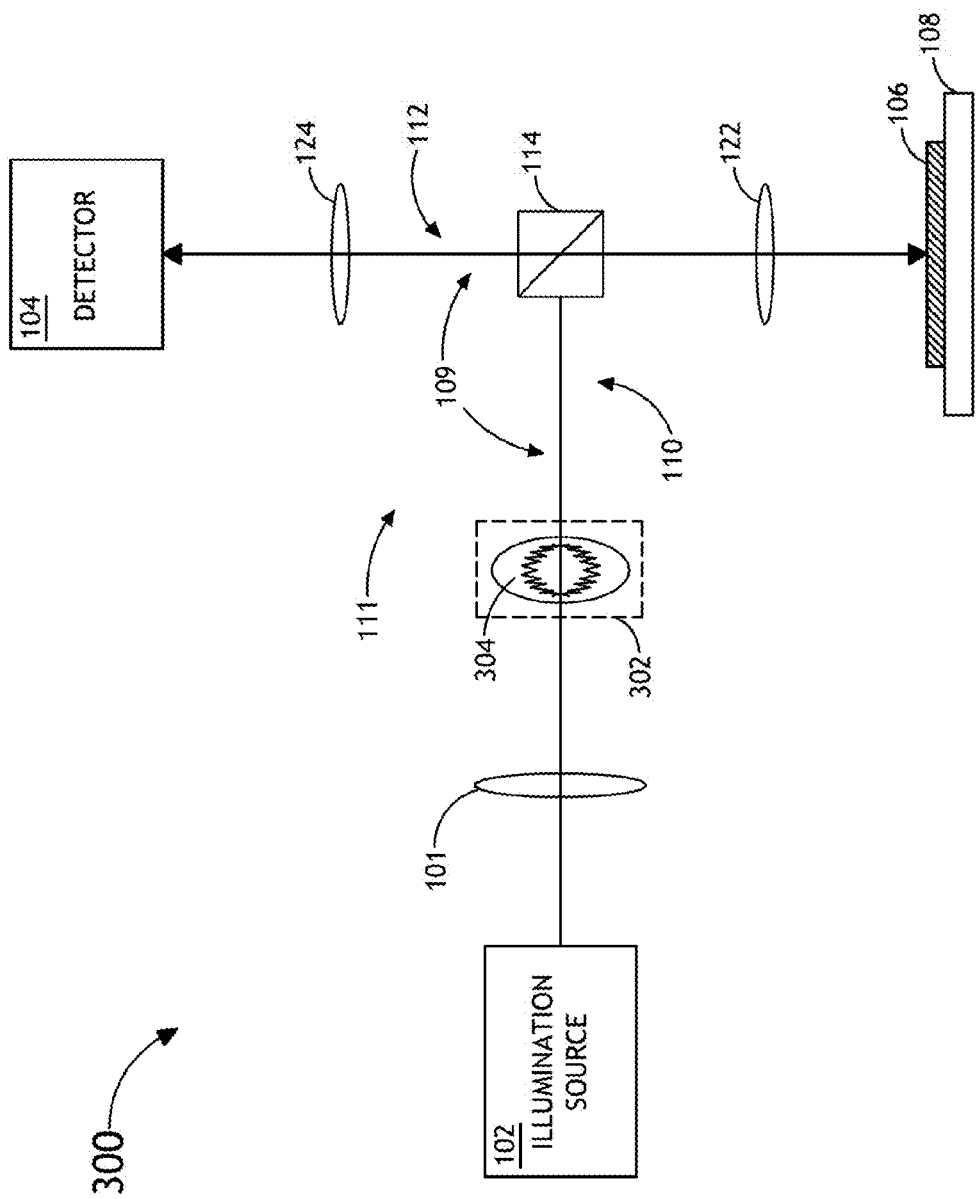
FIG. 3A is a simplified schematic view of a brightfield inspection system with a serrated aperture stop, in accordance with one embodiment of the present invention.
Figure 3B:
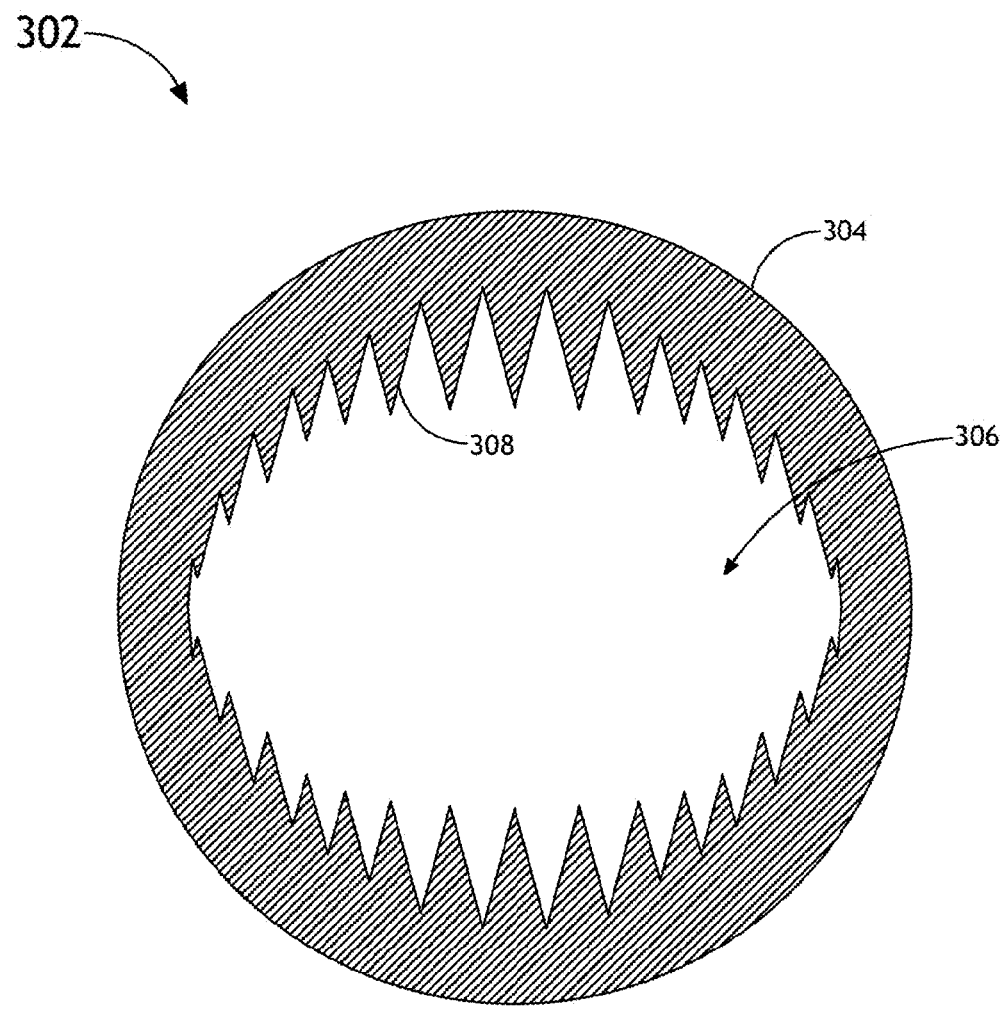
FIG. 3B is a schematic view of a serrated aperture stop, in accordance with one embodiment of the present invention.

FIGS. 3A-3B illustrate simplified schematic views of an inspection system 300 equipped with a serrated aperture assembly 302 configured as an aperture of the optical pathway 109 of the inspection system 300, in accordance with one embodiment of the present invention. The present embodiment is directed to the improvement of resolution in an optical inspection system (e.g., darkfield or brightfield inspection system). In particular, the present embodiment is directed to the enhancement of small defect detection near bright peripheral structures. In the present embodiment, improved system resolution is accomplished utilizing serrated aperture stops 304 configured as the aperture stop (e.g., illumination aperture, imaging aperture, or another aperture) of the inspection system 300 to produce a desired apodizing function. It is further noted herein that in addition to improved resolution, the softening of the aperture edges may reduce the aperture placement accuracy requirement. As a result, edge apodization may make system-to-system more straightforward.

It is recognized herein that the components and embodiments of inspection system 100 described previously herein should be interpreted to extend to inspection system 300 unless otherwise noted. In this sense, the inspection system 300 includes an illumination source 102 configured to illuminate a surface of a sample 106 disposed on a sample stage 108, a detector 104 configured to detect light emanating (e.g., scattered or reflected) from the surface of the sample 106. Further, the illumination source 102 (e.g., broadband source or narrowband source) and the detector 104 are optically coupled via an optical pathway 109 of an optical system 111.

In another aspect, the system 300 includes a serrated aperture assembly 302 disposed along the optical pathway 109 of the optical system 111 and configured as an aperture of the inspection system 300. In another aspect, the serrated aperture assembly 302 may include one or more serrated aperture stops 304, as shown in FIG. 3B. In one embodiment, the one or more serrated aperture stops 304 may be implemented as an illumination aperture stop. In this regard, the one or more serrated aperture stops 304 of the serrated aperture assembly 302 may be disposed along the illumination arm 110 and configured to pass a selected amount of light from the illumination source 102 to the surface of the sample 106. In another embodiment, the one or more serrated aperture stops 304 may be implemented as an imaging aperture stop. In this regard, the one or more serrated aperture stops 304 of the serrated aperture assembly 302 may be disposed along the collection arm 112.

The one or more serrated aperture stops 304 may include a serrated aperture 306 formed by a plurality of serration features 308 arranged about the aperture 306. The serrated aperture features are formed in a manner (e.g., pitch, size, and etc.) such that the serrated aperture 306 applies an apodization profile to illumination passing through the serrated aperture 306. In this regard, the one or more serrated aperture stops 304 may produce an apodized pupil function of illumination from illumination source 102.

The one or more serrated aperture stops 304 of the presented invention may be formed in any manner known in the art. In one embodiment, the one or more serrated aperture stops 304 are formed from a sheet metal plate. For example, a selected serrated aperture 306 may be cut out of a sheet metal plate in such a manner to form the serrated aperture stop 306 as shown in FIG. 3B. In another embodiment, the one or more serrated aperture stops 304 are formed by depositing a patterned layer of metal material (e.g., metal material opaque to illumination emitted by illumination source) onto a transparent substrate. For example, the metal used to form the patterned layer may include, but is not limited to, chrome. In a further embodiment, a patterned layer of chrome may be deposited onto any transparent (i.e., transparent to the illumination emitted by the illumination source) substrate known in the art. For example, the transparent substrate may include, but is not limited to, a glass substrate or a quartz-glass substrate.

In another embodiment, the patterned metal layer may be deposited onto the transparent substrate in any manner known in the art. For example, the patterned metal material may be deposited onto the substrate using a printing process. By way of another example, the patterned metal material may be deposited onto the substrate using an evaporation deposition process.

In another embodiment, the one or more serration features 308 of the one or more serrated aperture stops 304 may have a selected pitch. In a further embodiment, the selected pitch may be selected based on the aspect ratio of the imaging portion of the detector 104.

In one embodiment, the serrated aperture assembly 102 may include a single serrated aperture stop 304. In this regard, the arrangement of the serrated pattern features 308 of the single aperture stop may be such to produce the desired pupil apodization function. In this sense, a single serrated aperture stop 304 having serrated features 308 with a size, pitch, and position appropriate to produce the desired pupil apodization function may be implemented.

Figure 3C:
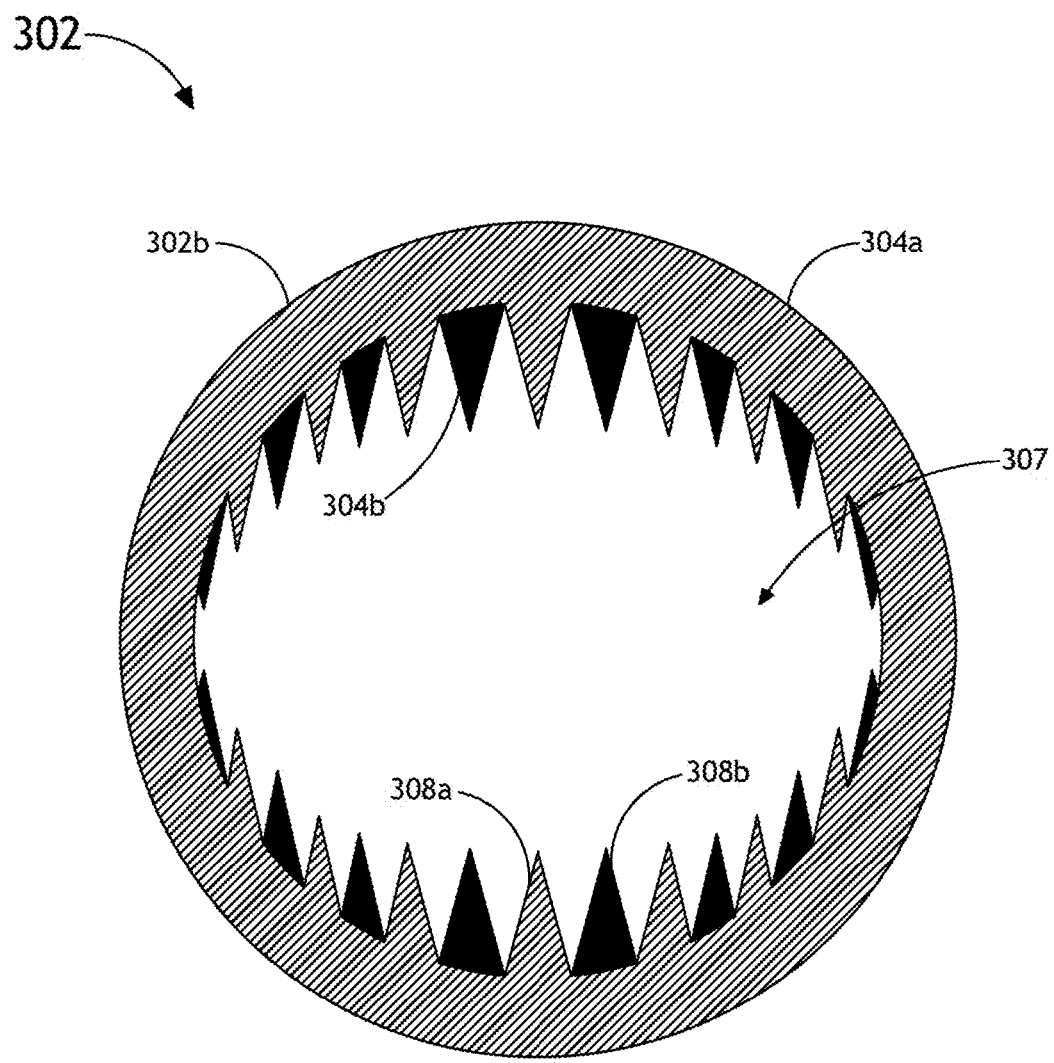
FIG. 3C is a schematic view of two serrated aperture stops in a stacked configuration to form a composite aperture, in accordance with one embodiment of the present invention.

As shown in FIG. 3C, the serrated aperture assembly 302 may include two or more serrated aperture stops 304a and 304b. In a further embodiment, the two or more serrated aperture stops may include a first serrated aperture 304a and a second serrated aperture stop 304b. In one embodiment, the first serrated aperture 304a and the at least a second serrated aperture stop 304b may be "stacked" or coupled together to form a composite serrated aperture stop, as shown in FIG. 3C.

In this regard, the first serrated aperture stop 304a is oriented with respect to the at least a second serrated aperture stop 304b in order to form a composite aperture 307. In one aspect, the composition pattern formed by the interleaving of the first set of serrated features 308a and the second set of serrated features 308b may act to achieve a selected pitch. In another aspect, the composition pattern formed by the interleaving of the first set of serrated features 308a and the second set of serrated features 308b may act to achieve the desired apodization profile. It is recognized herein that a multiple serrated aperture stop approach may aid in mitigating fabrication difficulties as it allows a user to more readily achieve a desired pitch and composite pattern feature.

In another embodiment, the one or more serrated apertures stops 304 of the serrated aperture assembly 302 may be selectably inserted into the optical pathway 109 of the inspection system 300. In this regard, the one or more serrated aperture stops 304 are selectably actuatable along a direction substantially perpendicular to the optical pathway 109. In one embodiment, the one or more serrated aperture stops 304 are disposed on an actuation stage (not shown) (e.g., translation stage and/or rotational stage) suitable for selectable placing the one or more serrated apertures into the illumination arm 110 or the collection arm 112 of the inspection system 300. In this regard, a control system may be communicatively coupled to the actuation stage and configured to selectably control the placement of the one or more serrated aperture stops 304. For example, the control system used to control the apodization imparted by the serrated apertures 306/307 may consist of the control system 114 described previously herein.

In another embodiment, the one or more serrated aperture stops 304 are disposed on a slidable stage (not shown) (e.g., translation stage and/or rotational stage) suitable for selectably placing the one or more serrated apertures into the illumination arm 110 or collection arm 112 of the inspection system 300. In this regard, a user may manually insert the one or more serrated aperture stops 304 into the illumination arm 110 or collection arm 112 of the inspection system 300. Alternatively, a user may manually remove the one or more serrated aperture stops 304 from the illumination arm 110 or the collection arm 112 of the inspection system 300.

Figure 3D:
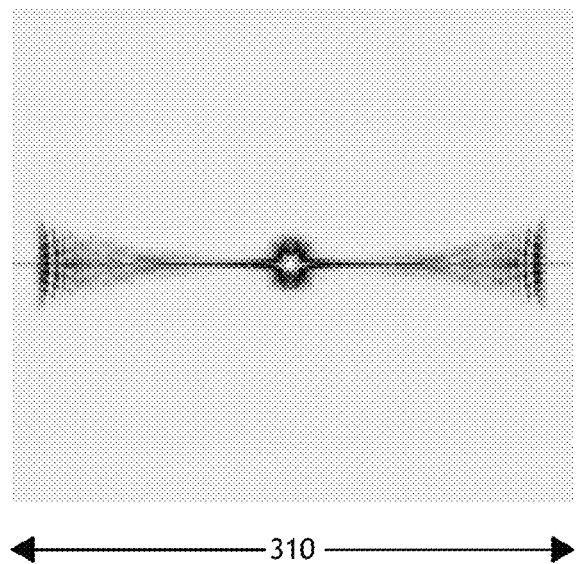
FIG. 3D is a schematic view of a diffraction pattern resulting from the application of a serrated aperture stop, in accordance with one embodiment of the present invention.
Figure 3E:
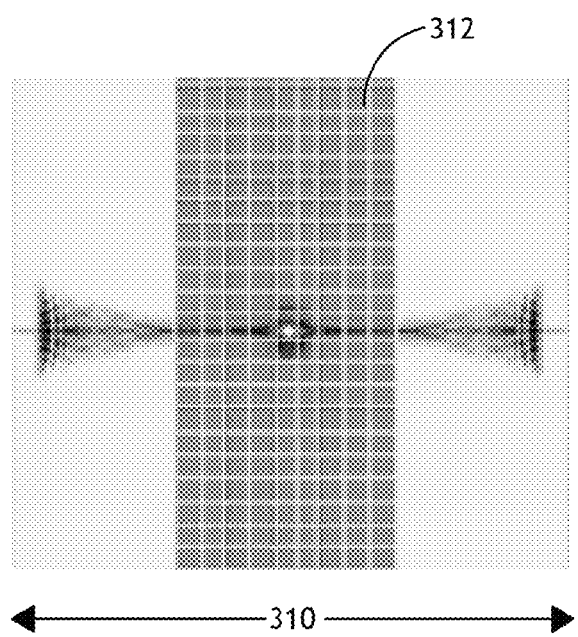
FIG. 3E is a schematic view of the positioning of the imaging portion of a detector to avoid the diffraction pattern resulting from the application of a serrated aperture stop, in accordance with one embodiment of the present invention.

In another aspect, the one or more serrated apertures 306 of the serrated aperture assembly 302 may have a selected orientation. In this regard, the orientation of the pattern formed by the one or more serrated features 308 is such that the diffraction resulting from the one or more serration features 308 (e.g., teeth) misses the imaging portion (e.g., CCD chip) of the detector 104. In one embodiment, as shown in FIG. 3D, the serrate aperture 306 having serrated features 308 as shown in FIG. 3B may generate diffraction orders along the horizontal direction 310. As such, in this serration feature 308 configuration, it is advantageous to place the imaging portion of the detector 104 such that the long axis is orientated vertically, as shown in FIG. 3E, thereby allowing the imaging portion of the detector 104 to avoid the generated diffraction orders.

Figure 3F:
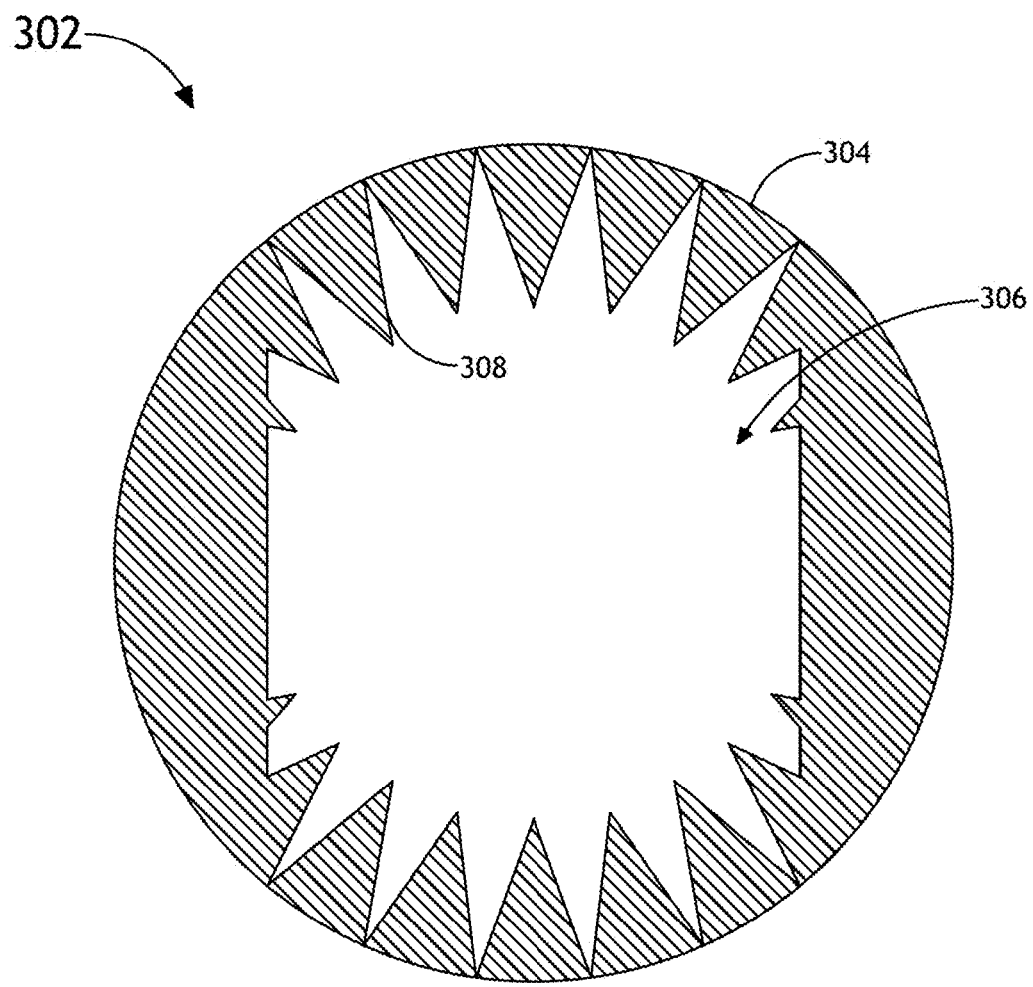
FIG. 3F is a schematic view of a serrated aperture stop with truncated serration features along one direction, in accordance with one embodiment of the present invention.
Figure 3G:
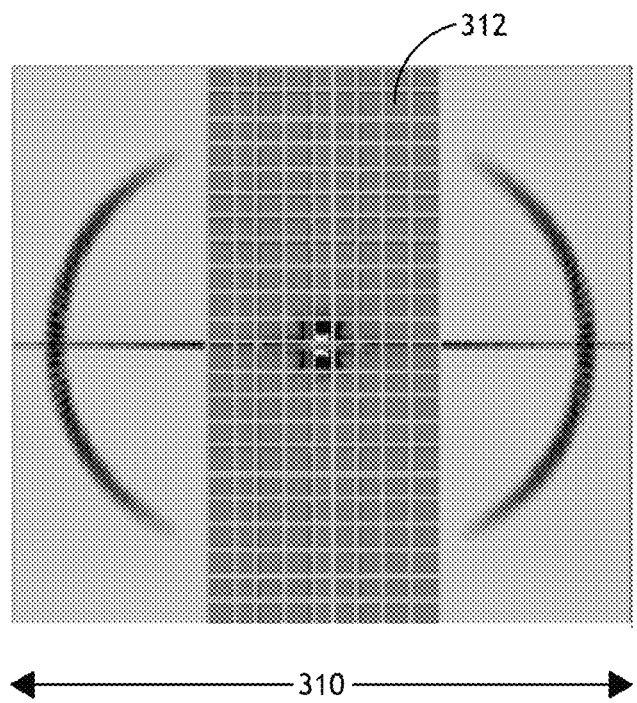
FIG. 3G is a schematic view of a diffraction pattern resulting from the application of a serrated aperture stop with truncated serration features along one direction, in accordance with one embodiment of the present invention.
Figure 4A:
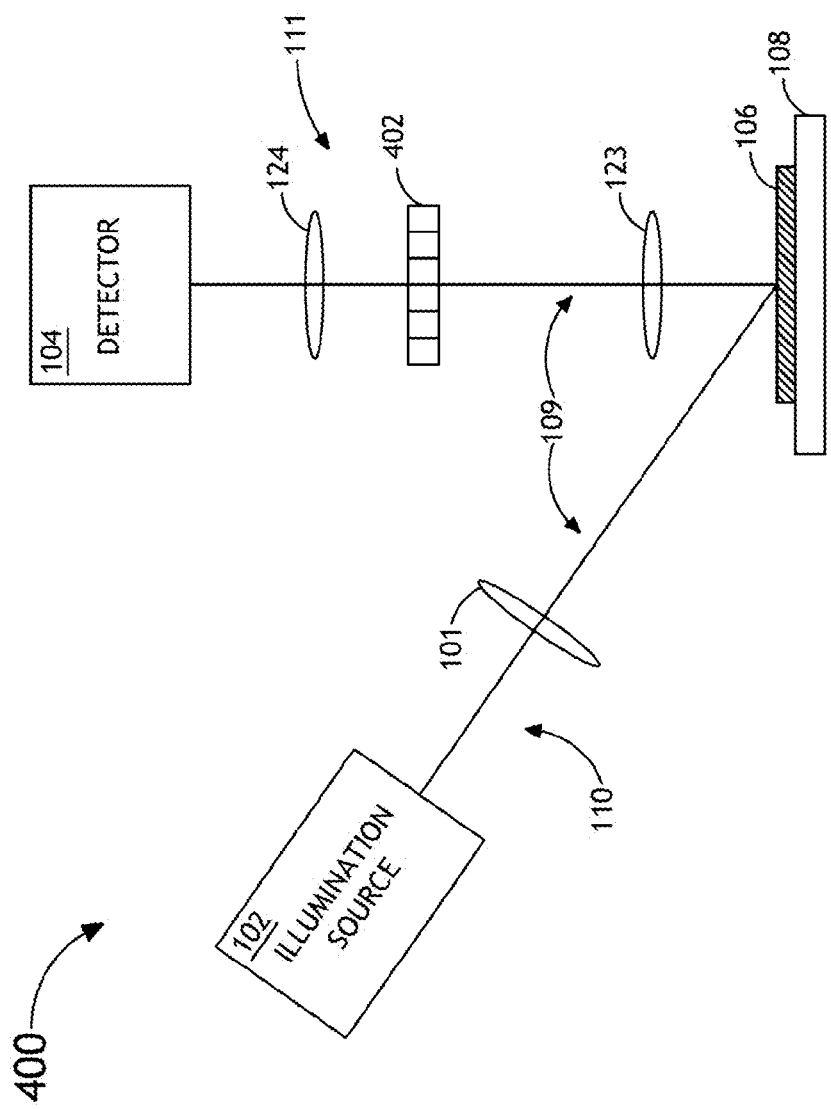
FIG. 4A is a simplified schematic view of a darkfield inspection system equipped with a Fourier filter having apodized edges, in accordance with one embodiment of the present invention.
Figure 4B:
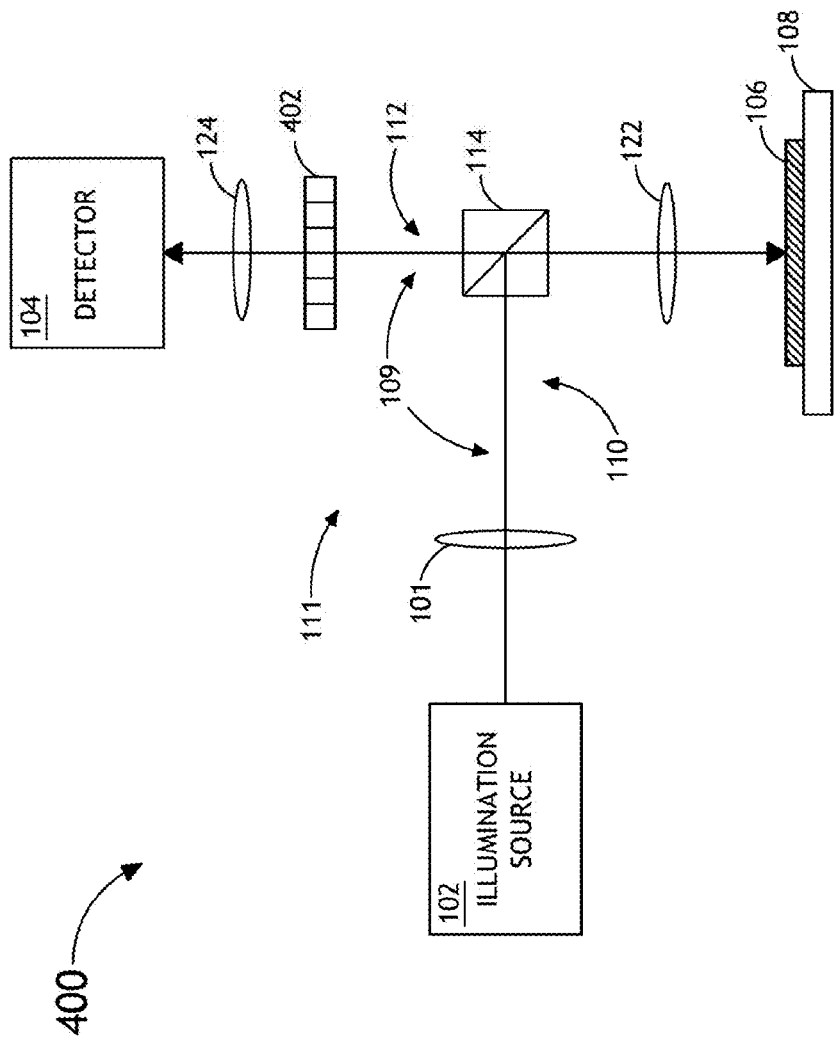
FIG. 4B is a simplified schematic view of a brightfield inspection system equipped with a Fourier filter having apodized edges, in accordance with one embodiment of the present invention.
Figure 4C:
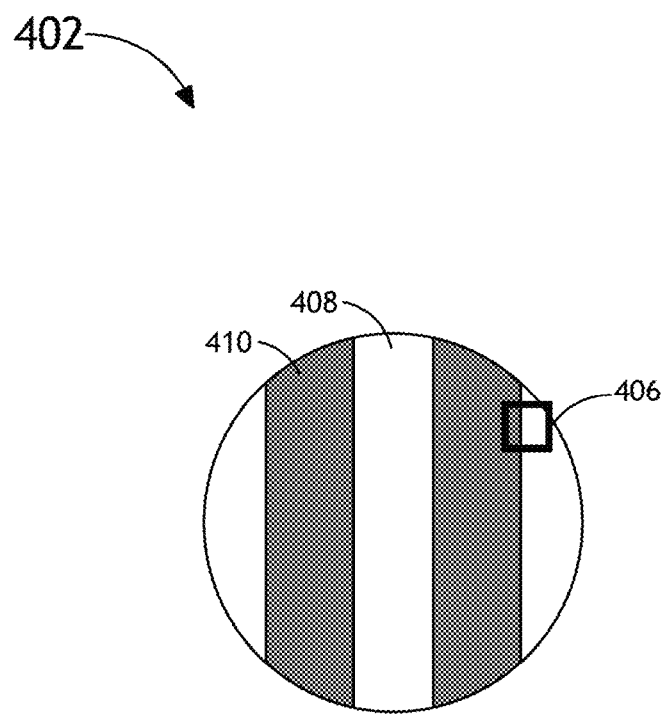
FIG. 4C is a schematic view of a Fourier filter having blocking elements with apodized edges suitable for implementation in the collection arm of an inspection system, in accordance with one embodiment of the present invention.
Figure 4D:
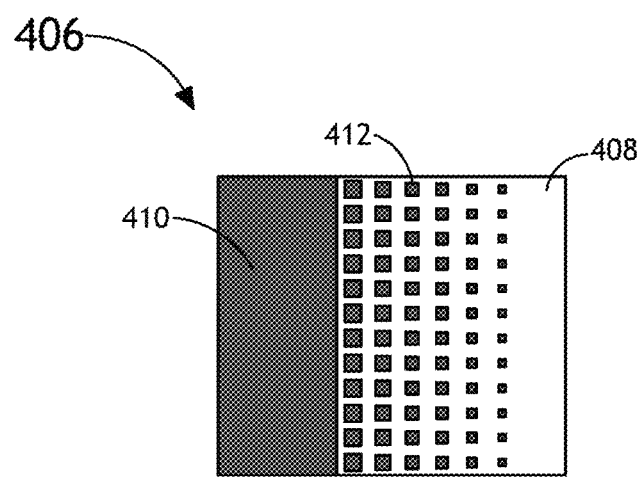
FIG. 4D is a schematic view of a variable dot density edge of a blocking element of a Fourier filter, in accordance with one embodiment of the present invention.
Figure 4E:
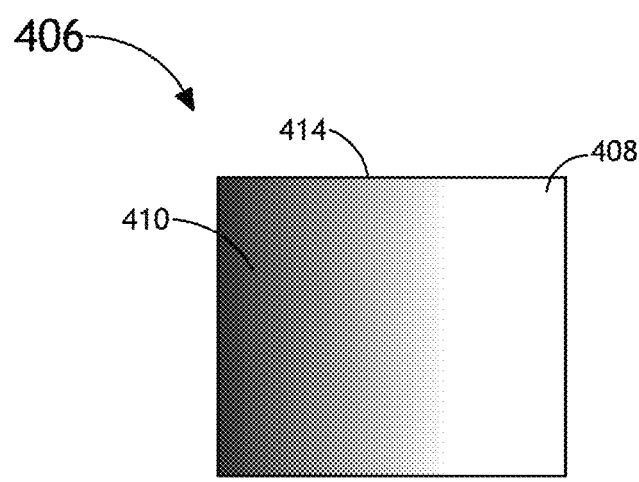
FIG. 4E is a schematic view of a graded coating edge of a blocking element of a Fourier filter, in accordance with one embodiment of the present invention.
Figure 4F:
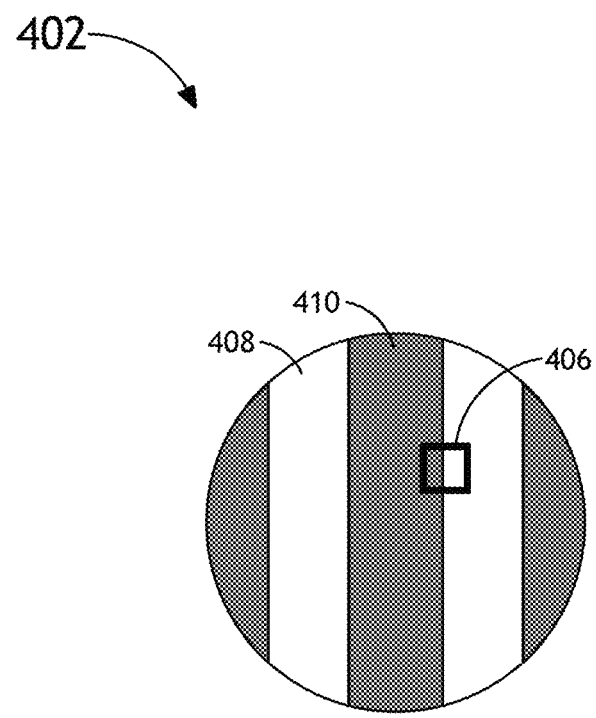
FIG. 4F is a schematic view of a Fourier filter having apodized edges suitable for implementation in the illumination arm of an inspection system, in accordance with one embodiment of the present invention.

In another embodiment, as shown in FIG. 3F, the serration features 308 may be positioned about the aperture 306 in a radial fashion, with the aperture 306 truncated at the horizontal edges. As shown in FIG. 3G, the truncation of the aperture 306 at the horizontal edges, allows the diffracted light to avoid the imaging portion of the detector 104.

In a further embodiment, the truncation as depicted in FIG. 3F may be accomplished utilizing additional opaque substrates (e.g., opaque plates) arranged to block a selected portion of the aperture 306. Further, the amount of truncation to impart to the aperture 306 may be selectable utilizing one or more actuation stages (e.g., motorized translation stage) in communication with a control system suitable for selectably controlling the actuation stage. For example, the control system used to control the truncation of the aperture 306 may consist of the control system 114 described previously herein.

FIGS. 4A-4F illustrate an inspection system 400 equipped with one or more Fourier filters 402 having blocking elements 410 with edge apodization, in accordance with one embodiment of the present invention.

The present embodiment is directed to a Fourier filter 402 including one of more blocking elements 410, whereby each blocking element is selectable to have a variable transmittance to illumination between 0 and 100%. In this manner, the blocking elements of the Fourier filter include edge regions that selectively block illumination using patterns providing graduated on/off filtering (as opposed to abrupt on/off filtering). Application of the edge apodized Fourier filter 402 of the present invention in the imaging path of the inspection system 400 acts to reduce edge ringing and the diffraction tails associated with patterns on the sample 106.

It is recognized herein that the components and embodiments of inspection system 100 and 300 described previously herein should be interpreted to extend to inspection system 400 unless otherwise noted. In this sense, the inspection system 400 includes an illumination source 102 configured to illuminate a surface of a sample 106 disposed on a sample stage 108, a detector 104 configured to detect light emanating (e.g., scattered) from defects from the surface of the sample 106. Further, the illumination source 102 (e.g., broadband source or narrowband source) and the detector 104 are optically coupled via an optical pathway 109 of an optical system 111. It is further noted that the Fourier filter 402 of the present invention may be implemented in a DF or BF inspection system setting.

In one aspect, the system 400 includes a Fourier filter 402 disposed along the optical pathway 109 of the optical system 111. In one embodiment, the Fourier filter 402 is disposed along the collection arm 112 of the inspection system 400. For example, the Fourier filter 402 may be disposed at the Fourier plane of the collection arm 112 of the inspection system 400. In this embodiment, the Fourier filter 402 is positioned at or near the imaging aperture of the collection arm 112. In this regard, the Fourier filter 402 is configured to block illumination reflected and/or diffracted from periodic features of sample 106.

In an alternative embodiment, the Fourier filter 402 may be disposed along the illumination arm 110 of the inspection system 400 (not shown).

In one aspect, the Fourier filter 402 of inspection system 400 includes one or more blocking elements 410 arranged in an array pattern in order to block a portion of illumination emanating from periodic structures of the surface of the sample. In one embodiment, the array pattern is a one-dimensional array. For example, the array pattern may include a series of parallel rectangular elements (or stripes) arranged to selectively block illumination from the surface of the sample 106. In one embodiment, the array pattern is a two-dimensional array (not shown). For example, the array pattern may include a rectangular array of blocking elements arranged to selectively block illumination from the surface of the sample 106.

In a further aspect, the one or more blocking elements 410 of the array pattern are arranged to block illumination diffracted or reflected from one or more periodic structures on the sample 106. In an additional aspect, the one or more blocking elements 410 of the array pattern are arranged to allow transmission of illumination scattered from one or more defects on the sample 106 via the transmission regions 408 of the filter 402.

The construction, positioning, and implementation of Fourier filters is described generally in U.S. Pat. No. 7,397,557, issued on Jul. 8, 2008; U.S. Pat. No. 6,020,957, issued on Feb. 1, 2000; U.S. Pat. No. 7,869,020, issued on Jan. 11, 2011; and U.S. Pat. No. 7,940,384, issued on May 10, 2011, which are each incorporated herein by reference in their entirety.

In an additional aspect, each of the one or more blocking elements 410 of the Fourier filter 402 includes one or more edge regions configured to provide a graduated transmission function to the illumination transmitted/block by the filter 402. The graduated edge regions of the blocking elements 410 are constructed to reduce the measured contribution from diffraction from patterned regions of the sample 106 and/or suppress ringing artifacts. In this regard, the edge regions of the blocking elements 410 provide for a gradual transition from a substantially 100% blocking state (e.g., center of blocking element) to a substantially 100% transmission state (e.g., center of transmission region 408). In a further embodiment, the particular configuration of the edge region results in a locally averaged transmission function of the Fourier filter that is an apodizing function.

In one embodiment, the edge region (shown by 406 in FIGS. 4A and 4B) may include a variable dot density pattern 412. In a further embodiment, the variable dot density pattern 412 may include a pattern of opaque features (e.g., dots, squares, and the like) that vary in size as a function of distance away from the fully opaque portion of the blocking element 410.

In this sense, the variable dot density pattern 412 may consist of alternating high and low transmittance areas, with the size of each low transmittance area (i.e., opaque features) shrinking as a function of distance from the blocking element until a region 408 of substantially 100% transmittance is attained. In another embodiment, the variable dot density pattern 412 may have a selected pitch. In a further embodiment, the pitch of the variable dot density features is selected (e.g., small enough) such that the diffraction orders resulting from the application of the filter 402 reside outside of the imaging field of view of the detector 104, thereby avoiding, or at least reducing, optical artifacts in the image plane. In another embodiment, the width and apodization profile are selected in a manner to at least partially suppress side lobes of the diffracted illumination without deteriorating the energy and width of the primary lobe. It is further noted herein the apodizing function of the filter 402 may consist of a superset of the locally averaged transmission function defined by alternating high transmittance areas and substantially opaque areas.

In another embodiment, a given blocking element 410 may be apodized along a first direction (e.g., X) and a second direction (e.g., Y). In this regard, the blocking element 410 may include a first edge region aligned on a horizontal portion of the blocking element 410 and a second edge region aligned on a vertical portion of the blocking element 410. In this sense, the first region may include a variable dot density pattern having a first selected pitch, while the second region includes a second variable dot density pattern having a second selected pitch.

In another embodiment, a variable dot density pattern may be formed by patterning an optically opaque thin coating on the surface of a transparent mechanically stable substrate. It is recognized herein that the variable dot density pattern may be formed using any patterning technique known in the art, such as, but not limited to, lithographic printing (e.g., e-beam lithography, optical lithography, or interference lithography). Alternatively, the variable dot density pattern of the Fourier filter 402 may be formed using patterned UV curable ink or direct laser writing. In another embodiment, the variable dot density pattern may be formed with one or more selectively reflective MEMs devices, whereby transmission/opaque regions are formed using the transmission/reflection elements of an MEM device.

In an alternative embodiment, the edge region (shown by 406 in FIGS. 4A and 4B) may include a graded coating 414 having a thickness or composition gradient as a function of distance from the one or more blocking elements 410. In a further embodiment, the graded film is configured to provide an apodizing function as described previously herein. For example, the thickness of the coating may become thinner as a function of distance from the one or more blocking regions 410, thereby resulting in an edge region with diminishing opaqueness as a function of increasing distance from the blocking regions 410, until a substantially transparent region 408 is attained. By way of another example, the composition of the coating may be such that the coating becomes increasingly transparent as a function of increasing distance from the one or more blocking regions 410, thereby resulting in an edge region with diminishing opaqueness as a function of increasing distance from the blocking regions 410, until a substantially transparent region 408 is attained. The graded coating may be deposited using any thin film coating technology known in the art, such as, but not limited to, sputtering deposition or evaporation.

In one embodiment, the Fourier filter with edge apodization 402 may be formed by depositing a metal onto a glass substrate. Any metal and any substrate known in the art may be used to form the Fourier filter of the present invention. For example, the Fourier filter with edge apodization 402 may be formed by depositing chrome (e.g., depositing dot array or depositing graded coating) on a glass substrate. In another embodiment, in the case of the variable dot pattern of FIG. 4D, the array may be configured to apply a half-wave cosine transmission profile given by:

$$T_c(x) = \frac{1}{2}\left(1 - \cos\frac{\pi x}{L}\right)$$

where Tc is the transmission profile and x is the position along the apodization length, L. In a further embodiment, the fill factor for the apodized edge may consist of the following:

$$\frac{Area_m(x)}{Area_T} = 1 - \sqrt{\frac{1}{2}\left(1 - \cos\frac{\pi x}{L}\right)}$$

where $Area_m$ is the area of the metal opaque features (e.g., chrome features) and $Area_T$ is the total cell area.

The total apodization length may take on various lengths. For instance, the length may range from approximately 100 to 1000 µm. The pitch of the opaque features in the variable dot density pattern may take on various sizes. For instance, the pitch of features may range from approximately 1 to 10 µm. The size of individual opaque features may also take on various sizes, ranging from 0.1 to 10 µm. The step size with which adjacent opaque features varies may be on the order of 0.05 to 1 µm. It is noted herein that the above transmission profile and dimensions are not in any way limiting and should be interpreted merely as illustrative.

In another embodiment, the Fourier filter 402 with edge apodization may be selectably inserted into the optical pathway 109 of the inspection system 400. In this regard, the Fourier filter 402 is selectably actuatable along a direction substantially perpendicular to the optical pathway 109. In one embodiment, the Fourier filter 402 is disposed on an actuation stage (not shown) (e.g., translation stage and/or rotational stage) suitable for selectably placing the Fourier filter 402 into the collection arm 112 of the inspection system 400. In this regard, a control system may be communicatively coupled to the actuation stage and configured to selectably control the placement of the Fourier filter 402. For example, the control system used to control the filtering and apodization imparted by the Fourier filter 402 may consist of the control system 114 described previously herein.

In another embodiment, the Fourier filter 402 is disposed on a slidable stage (not shown) (e.g., translation stage and/or rotational stage) suitable for selectably placing the Fourier filter 402 into the optical pathway 109 (e.g., collection arm 112) of the inspection system 400. In this regard, a user may manually insert the Fourier filter 402 into the imaging system of the inspection system 400. Alternatively, a user may manually remove the Fourier filter 402 from the imaging system of the inspection system 400.

All of the methods described herein may include storing results of one or more steps of the method embodiments in a storage medium. The results may include any of the results described herein and may be stored in any manner known in the art. The storage medium may include any storage medium described herein or any other suitable storage medium known in the art. After the results have been stored, the results can be accessed in the storage medium and used by any of the method or system embodiments described herein, formatted for display to a user, used by another software module, method, or system, etc. Furthermore, the results may be stored "permanently," "semi-permanently," temporarily, or for some period of time. For example, the storage medium may be random access memory (RAM), and the results may not necessarily persist indefinitely in the storage medium.

Although particular embodiments of this invention have been illustrated, it is apparent that various modifications and embodiments of the invention may be made by those skilled in the art without departing from the scope and spirit of the foregoing disclosure. Accordingly, the scope of the invention should be limited only by the claims appended hereto. It is believed that the present disclosure and many of its attendant advantages will be understood by the foregoing description, and it will be apparent that various changes may be made in the form, construction and arrangement of the components without departing from the disclosed subject matter or without sacrificing all of its material advantages. The form described is merely explanatory, and it is the intention of the following claims to encompass and include such changes.

What is claimed:

1. An inspection system with selectable apodization, comprising:
    an illumination source configured to illuminate a surface of a sample disposed on a sample stage;
    a detector configured to detect at least a portion of light emanating from the surface of the sample, the illumination source and the detector being optically coupled via an optical pathway of an optical system including an illumination arm and a collection arm; and
    a selectably configurable apodization device disposed along the optical pathway of the optical system, wherein the apodization device includes one or more apodization elements operatively coupled to one or more actuation stages, the one or more actuation stages configured to selectably actuate the one or more apodization elements along one or more directions in order to apply a selected apodization profile.

2. The inspection system of claim 1, wherein the illumination source comprises:
    at least one broad band illumination source.

3. The inspection system of claim 1, wherein the illumination source comprises:
    at least one narrow band illumination source.

4. The inspection system of claim 1, wherein the inspection system is configured as a bright-field inspection system.

5. The inspection system of claim 1, wherein the inspection system is configured as a dark-field inspection system.

6. The inspection system of claim 1, wherein the one or more actuation stages of the selectably configurable apodization device comprises:
    one or more translational stages.

7. The inspection system of claim 1, wherein the one or more actuation stages of the selectably configurable apodization device comprises:
    one or more rotational stages.

8. The inspection system of claim 1, wherein the one or more actuation stages of the selectably configurable apodization device are configured to selectably actuate one or more apodization elements into the optical pathway of the optical system.

9. The inspection system of claim 1, wherein the one or more apodization elements comprises:
    two or more apodization elements.

10. The inspection system of claim 1, wherein the one or more apodization elements comprises:
    a single apodization element.

11. The inspection system of claim 1, wherein the one or more apodization elements operatively coupled to on one or more actuation stages comprises:
    a first apodization element disposed on a first actuation stage and at least a second apodization element disposed on at least a second actuation stage.

12. The inspection system of claim 1, wherein the one or more apodization elements comprise:
    one or more variable dot density apodizers.

13. The inspection system of claim 1, wherein the one or more apodization elements include one or more neutral density coating apodizers.

14. The inspection system of claim 1, wherein the one or more apodization elements include one or more serrated plates.

15. The inspection system of claim 1, wherein the one or more apodization elements include one or more Fourier filters having one or more blocking elements, the one or more blocking elements including one or more apodized edges.

16. The inspection system of claim 1, wherein the one or more apodization elements are configured to apply a first selected apodization profile along a first direction and at least a second selected apodization profile along a second direction.

17. The inspection system of claim 1, wherein the selected apodization profile comprises:
   at least one of a Gaussian profile, a cosine profile, or a Super Gaussian profile.

18. The inspection system of claim 1, wherein the selected apodization profile is a function of one or more pattern features of the sample.

19. An inspection system suitable for providing apodization, comprising:
   an illumination source configured to illuminate a surface of a sample disposed on a sample stage;
   a detector configured to detect at least a portion of light emanating from the surface of the sample;
   an optical system including an optical pathway configured to optically couple the illumination source and the detector; and
   a serrated aperture assembly disposed along the optical pathway of the optical system and configured as an aperture of the optical system, the serrated aperture assembly including one or more serrated aperture stops, wherein at least some of the one or more serrated aperture stops include a plurality of serration features, the one or more serrated aperture stops including a serrated pattern having a selected orientation, wherein the one or more serrated aperture stops apply a selected apodization profile to illumination transmitted along the optical pathway of the optical system.

20. The inspection system of claim 19, wherein the two or more serrated aperture stops include one or more sheet metal plates including a serrated aperture.

21. The inspection system of claim 19, wherein the two or more serrated aperture stops include one or more patterned metallic material layers deposited on a transparent substrate forming a serrated aperture.

22. The inspection system of claim 19, wherein the plurality of serration features of one or more of the serrated aperture stops are arranged with a selected pitch.

23. The inspection system of claim 22, wherein the selected pitch of the plurality of serration features of one or more of the serrated aperture stops is a function of an aspect ratio of the detector.

24. The inspection system of claim 22, wherein each of the plurality of serrations features has a selected size.

25. The inspection system of claim 19, wherein the one or more serrated aperture stops comprise:
   a first serrated aperture stop;
   at least a second serrated aperture stop operatively coupled to the first serrated aperture stop, wherein the first serrated aperture stop is oriented with respect to the at least a second serrated aperture stop in order to achieve a selected pitch.

26. The inspection system of claim 19, wherein the one or more serrated aperture stops comprise:
   a first serrated aperture stop;
   at least a second serrated aperture stop operatively coupled to the first serrated aperture stop, wherein the first serrated aperture stop is oriented with respect to the at least a second serrated aperture stop in order to achieve the apodization profile.

27. The inspection system of claim 19, wherein the selected orientation of the serrated pattern produces diffraction orders substantially along a first direction.

28. The inspection system of claim 27, wherein an axis of the detector is orientated along a second direction perpendicular to the first direction.

29. An inspection system suitable for providing apodization of illumination, comprising:
   an illumination source configured to illuminate a surface of a sample disposed on a sample stage;
   a detector configured to detect at least a portion of light emanating from the surface of the sample;
   an optical system including an optical pathway configured to optically couple the illumination source and the detector;
   a Fourier filter disposed along the optical pathway of the optical system, wherein the Fourier filter includes one or more illumination blocking elements arranged in an array pattern, wherein the one or more illumination blocking elements are arranged to block a portion of illumination from the sample, wherein one or more edge regions of the illumination blocking elements have a graduated transmission function, wherein a locally averaged transmission function of the Fourier filter is an apodizing function.

30. The inspection system of claim 29, wherein the Fourier filter includes one or more patterned metallic material layers deposited on a transparent substrate.

31. The inspection system of claim 29, wherein the one or more edge regions are defined by a thin film coating having a transmittance gradient.

32. The inspection system of claim 29, wherein the one or more edge regions are defined by a variable dot density pattern having a transmittance gradient.

33. The inspection system of claim 32, wherein the variable dot density pattern is formed on a transparent material.

34. The inspection system of claim 32, wherein the variable dot density pattern is formed on the transparent material via a lithographic process.

35. The inspection system of claim 34, wherein the variable dot density pattern is formed on a transparent material via a lithographic process, wherein the lithographic process includes etching away one or more portions of a metallic material layer formed on the transparent material.

36. The inspection system of claim 32, wherein the variable dot density pattern has a selected pitch along at least one direction.

37. The inspection system of claim 36, wherein the selected pitch along at least one direction of the variable dot density pattern is such that substantially all non-zero order diffraction orders reside outside of an imaging portion of the detector.

38. The inspection system of claim 36, wherein the variable dot density pattern has a first selected pitch along a first direction and a second selected pitch along a second direction.

39. The inspection system of claim 29, wherein the one or more blocking elements of the Fourier filter are arranged to block light from periodic structures of the sample.

40. The inspection system of claim 29, wherein the one or more blocking elements of the Fourier filter are arranged to block light scattered from the surface of the sample along a selected direction.

41. The inspection system of claim 29, wherein the one or more blocking elements of the Fourier filter are arranged to block undesired light scattered from the surface of the sample.

42. The inspection system of claim 29, wherein the one or more blocking elements of the Fourier filter are arranged to transmit light from non-periodic structures of the sample.

43. The inspection system of claim 29, wherein the one or more blocking elements are arranged in at least one of a one-dimensional array or a two-dimensional array.

44. The inspection system of claim 29, wherein the Fourier filter is positioned in at least one of a collection arm or an illumination arm of the optical system.

45. The inspection system of claim 29, wherein the Fourier filter is positioned at a Fourier plane of the optical system.

46. A system for providing selectable apodization in an optical system, comprising:
 a selectably configurable apodization device disposed along the optical pathway of the optical system, wherein the apodization device includes one or more apodization elements operatively coupled to one or more actuation stages, the one or more actuation stages configured to selectably actuate the one or more apodization elements along one or more directions; and
 a control system communicatively coupled to the one or more actuation stages, wherein the control system is configured to selectably control an actuation state of at the one or more apodization elements, the selected apodization profile formed with the one or more apodization elements.

* * * * *